United States Patent
Mikule et al.

(10) Patent No.: US 11,661,453 B2
(45) Date of Patent: May 30, 2023

(54) COMBINATION THERAPIES FOR TREATING CANCER WITH NIRAPARIB AND PD-1 INHIBITORS

(71) Applicant: Tesaro, Inc., Waltham, MA (US)

(72) Inventors: Keith W. Mikule, Waltham, MA (US); Kaiming Sun, Waltham, MA (US); Jing Yu Wang, Waltham, CA (US); Zebin Wang, Waltham, MA (US)

(73) Assignee: Tesaro, Inc., Wilmington, DE (US)

( * ) Notice: Subject to any disclaimer, the term of this patent is extended or adjusted under 35 U.S.C. 154(b) by 234 days.

(21) Appl. No.: 16/651,920

(22) PCT Filed: Sep. 28, 2018

(86) PCT No.: PCT/US2018/053542
§ 371 (c)(1),
(2) Date: Mar. 27, 2020

(87) PCT Pub. No.: WO2019/067978
PCT Pub. Date: Apr. 4, 2019

(65) Prior Publication Data
US 2020/0299387 A1    Sep. 24, 2020

Related U.S. Application Data

(60) Provisional application No. 62/654,024, filed on Apr. 6, 2018, provisional application No. 62/578,298, filed (Continued)

(51) Int. Cl.
*C07K 16/28* (2006.01)
*A61P 35/00* (2006.01)
(Continued)

(52) U.S. Cl.
CPC ........ *C07K 16/2818* (2013.01); *A61K 9/0053* (2013.01); *A61K 39/3955* (2013.01);
(Continued)

(58) Field of Classification Search
CPC .................. A61P 35/00; A61K 9/0053; A61K 39/3955; A61K 2039/545; C07K 2317/76
See application file for complete search history.

(56) References Cited

U.S. PATENT DOCUMENTS 7,595,048 B2   9/2009   Honjo et al.
8,071,623 B2   12/2011  Jones et al.
(Continued)

FOREIGN PATENT DOCUMENTS

CN   110831580   2/2020
EA   201992594   3/2020
(Continued)

OTHER PUBLICATIONS

Alberts et al., Molecular Biology of the Cell, 4th edition. New York: Garland Science, at p. 2. (Year: 2002).*
(Continued)

*Primary Examiner* — Elly-Gerald Stoica
(74) *Attorney, Agent, or Firm* — Fish & Richardson P.C.

(57) ABSTRACT

The present invention provides methods of treatment for cancer through combination therapy with an agent that inhibits programmed death-1 protein (PD-1) signaling and an agent that inhibits poly[ADP-ribose] polymerase (PARP) signaling.

6 Claims, 6 Drawing Sheets

Specification includes a Sequence Listing.

Related U.S. Application Data on Oct. 27, 2017, provisional application No. 62/566,398, filed on Sep. 30, 2017.

(51) Int. Cl.
    *A61K 39/395*    (2006.01)
    *A61K 39/00*     (2006.01)
    *A61K 9/00*      (2006.01)

(52) U.S. Cl.
    CPC ........ *A61K 39/39558* (2013.01); *A61P 35/00* (2018.01); *A61K 2039/545* (2013.01); *C07K 2317/76* (2013.01)

(56) References Cited

U.S. PATENT DOCUMENTS

| | | |
|---|---|---|
| 8,217,149 B2 | 7/2012 | Irving et al. |
| 8,436,185 B2 | 5/2013 | Foley et al. |
| 8,728,474 B2 | 5/2014 | Honjo et al. |
| 8,779,108 B2 | 7/2014 | Queva et al. |
| 8,952,136 B2 | 2/2015 | Carven et al. |
| 9,624,298 B2 | 4/2017 | Nastri et al. |
| 9,707,302 B2 | 7/2017 | Goldenberg et al. |
| 9,815,897 B2* | 11/2017 | King ............... A61P 31/04 |
| 10,738,117 B2* | 8/2020 | King ............... A61P 35/00 |
| 2009/0123419 A1 | 5/2009 | Sherman et al. |
| 2010/0003192 A1 | 1/2010 | Sherman et al. |
| 2012/0207856 A1 | 8/2012 | Ajay et al. |
| 2012/0269861 A1 | 10/2012 | Sherman et al. |
| 2015/0071910 A1 | 3/2015 | Kowanetz et al. |
| 2015/0344968 A1 | 12/2015 | Johnson |
| 2016/0075783 A1* | 3/2016 | King ............... C07K 16/28 424/133.1 |
| 2016/0296633 A1 | 10/2016 | Goldenberg et al. |
| 2016/0340428 A1 | 11/2016 | Yang |
| 2017/0000885 A1 | 1/2017 | Rhee et al. |
| 2017/0049767 A1 | 2/2017 | Blanchette et al. |
| 2018/0311224 A1 | 11/2018 | Hedley et al. |
| 2020/0016142 A1 | 1/2020 | McGurk et al. |
| 2020/0017462 A1 | 1/2020 | Wu et al. |
| 2020/0055837 A1 | 2/2020 | Stewart et al. |
| 2020/0289493 A1 | 9/2020 | Bobilev et al. |
| 2020/0306236 A1 | 10/2020 | Mikule |
| 2021/0008053 A1 | 1/2021 | Sun et al. |
| 2021/0106574 A1 | 4/2021 | Feng et al. |
| 2022/0048983 A1 | 2/2022 | Milenkova-Ilieva et al. |

FOREIGN PATENT DOCUMENTS

| | | |
|---|---|---|
| EP | 0325199 | 10/1993 |
| EP | 0357061 | 6/1994 |
| EP | 2007733 | 5/2016 |
| EP | 3621592 | 3/2020 |
| JP | 2011509252 | 3/2011 |
| JP | 2011509253 | 3/2011 |
| JP | 2017504623 | 2/2017 |
| WO | WO 2007/113596 | 10/2007 |
| WO | WO 2008/084261 | 7/2008 |
| WO | WO 2009/064738 | 5/2009 |
| WO | WO 2009/087381 | 7/2009 |
| WO | WO 2010/091140 | 8/2010 |
| WO | WO 2011/153383 | 12/2011 |
| WO | WO 2011/160063 | 12/2011 |
| WO | WO 2012/027224 | 3/2012 |
| WO | WO 2013/182645 | 12/2013 |
| WO | WO 2014/088983 | 6/2014 |
| WO | WO 2014/088984 | 6/2014 |
| WO | WO 2014/138101 | 9/2014 |
| WO | WO 2014/179664 | 11/2014 |
| WO | WO 2015/086473 | 6/2015 |
| WO | WO 2015/108986 | 7/2015 |
| WO | WO 2015/116868 | 8/2015 |
| WO | WO 2015/184145 | 12/2015 |
| WO | WO 2016/094391 | 6/2016 |
| WO | WO 2016/126858 | 8/2016 |
| WO | WO 2016/161270 | 10/2016 |
| WO | WO 2016/200835 | 12/2016 |
| WO | WO 2016/210108 | 12/2016 |
| WO | WO 2017/075091 | 5/2017 |
| WO | WO 2017/142871 | 8/2017 |
| WO | WO 2018/005818 | 1/2018 |
| WO | WO 2018/059437 | 4/2018 |
| WO | WO 2018/085468 | 5/2018 |
| WO | WO 2018/085469 | 5/2018 |
| WO | WO 2018/129553 | 7/2018 |
| WO | WO 2018/129559 | 7/2018 |
| WO | WO 2018/200517 | 11/2018 |
| WO | WO 2018/201096 | 11/2018 |
| WO | WO 2018/208968 | 11/2018 |
| WO | WO 2018/213732 | 11/2018 |
| WO | WO 2019/005762 | 1/2019 |
| WO | WO 2019/067634 | 4/2019 |
| WO | WO 2019/067978 | 4/2019 |
| WO | WO 2019/071123 | 4/2019 |
| WO | WO 2019/133697 | 7/2019 |
| WO | WO 2019/152989 | 8/2019 |

OTHER PUBLICATIONS

Edwards et al., J Mol Biol 334:103-118 (Year: 2003).*
Marchalonis et al., Dev & Comp Immunol 30:223-247 (Year: 2006).*
Lippow et al., "Computational design of antibody-affinity improvement beyond in vivo maturation," Nature Biotechnology, 25(10): 1171-1176. (Year: 2007).*
Almagro & Franssen, Frontiers in Bioscience; 13:1619-33 (Year: 2008).*
Mendes-Pereira, A. "Synthetic lethal targeting of PTEN mutant cells with PARP inhibitors." EMBO Molecular Medicine, 315-322. (Year: 2009).*
Altshuler et al., "Generation of Recombinant Antibodies and Means for Increasing Their Affinity," Biochemistry (Moscow), 75(13): 1584-1605. (Year: 2010).*
Dedes et al. "Synthetic lethality of PARP inhibition in cancers lacking BRCA1 and BRCA2 mutations." Cell Cycle, 1192-1199 (Year: 2011).*
Wilcoxen et al. "Homologous recombination deficiency (HRD) score enriches for niraparib sensitive high grade ovarian tumors." Abstract #5532 Presented at ASCO (Year: 2015).*
ClinicalTrials.gov, "The Safety, Pharmacokinetics and Antitumor Activity of BGB-A317 in Combination With the BGB-290 in Subjects With Advanced Solid Tumors," U.S. National Library of Medicine, Aug. 13, 2017, retrieved from URL https://clinicaltrials.gov/ct2/history/NCT02660034?V_4=View#StudyPageTop,16 pgs. (Year: 2016).*
AlHilli et al. "In vivo anti-tumor activity of the PARP inhibitor niraparib in homologous." Gynecologic Oncology, 379-388 (Year: 2016).*
CAS Registry No. 2022215-59-2 Substance Detail, CAS SciFinder, pp. 1-5 (Year: 2016).*
Konstantinopoulos et al., "Phase I/II study of niraparib plus pembrolizumab in patients with triple-negative breast cancer or recurrent ovarian cancer," Meeting Abstract | 2016 ASCO Annual Meeting, re-printed in Journal of Clinical Oncology 34(15), Suppl. (Year: 2016).*
Dockery et al. "Rucaparib: the past, present, and future of a newly approved PARP inhibitor for ovarian cancer." Onco Targets Ther, 3029-3037 (Year: 2017).*
Freidlander et al. "A Phase 1/1b Study of the Anti-PD-1 Monoclonal Antibody BGB-A317 (A317) in Combination with the PARP Inhibitor BGB-290 (290) in Advanced Solid Tumors," American Society of Clinical Oncology (Year: 2017).*
Hasegawa et al., "Single amino acid substitution in LC-CDR1 induces Russell body phenotype that attenuates cellular protein synthesis through eIF2a phosphorylation and thereby downregulates IgG secretion despite operational secretory pathway traffic," MABS, vol. 9, No. 5, pp. 854-873 (Year: 2017).*

(56) References Cited

OTHER PUBLICATIONS

Sulea et al., "Application of Assisted Design of Antibody and Protein Therapeutics (ADAPT) improves efficacy of a Clostridium difficile toxin A single-domain antibody," Scientific Reports, 8(260):1-11. (Year: 2018).*
Marks et al., "How repertoire data are changing antibody science," J. Biol. Chem. 295(29) 9823-9837 (Year: 2020).*
Vajda et al., "Progress toward improved understanding of antibody maturation," Current Opinion in Structural Biology, 67 pp. 226-231 (Year: 2021).*
Akbar et al., Cell Reports 34, 108856, at p. 2 (Year: 2021).*
Lo et al., "Conformational epitope matching and prediction based on protein surface spiral features," BMC Genomics vol. 22, Article No. 116 (Year: 2021).*
Morales et al., Review of poly (ADP-ribose) polymerase (PARP) mechanisms of action and rationale for targeting in cancer and other diseases. Crit. Rev. Eukaryot. Gene Expr. 24, 15-28, 2014. (Year: 2014).*
Stolze et al., Comparative analysis of KRAS codon 12 , 13 , 18, 61 , and 117 mutations using human MCF10A isogenic cell lines. Sci Rep 5, 8533, 2015. (Year: 2015).*
Yehia et al., The Clinical Spectrum of PTEN Mutations. Annu. Rev. Med. 71, 103-16, 2020. (Year: 2020).*
[No author listed] "Integrated genomic analyses of ovarian carcinoma," Nature, 2011, 474:609-15.
Adams et al, "Phase 2 study of pembrolizumab (pembro) monotherapy for previously treated metastatic triple-negative breast cancer (mTNBC): Keynote-086 cohort A", Journal of Clinical Oncology, May 2017, 35(15)1008 (abstract only).
Agata et al., "Expression of the PD-1 antigen on the surface of stimulated mouse T and B lymphocytes", International Immunology, May 1996, 8(5):765-772.
American Cancer Society. Cancer Facts & Figures 2016. Atlanta: American Cancer Society 2016; retrieved on Oct. 26, 2020, retrieved from URL: http://www.cancer.org/acs/groups/content/@research/documents/document/acspc-047079,pdf, 3 pages.
Andreae et al., "Maturation and activation of dendritic cells induced by lymphocyte activation gene-3 (CD223)," J. Immunol., 2002, 168:3874-3880.
Anonymous, "History of Changes for Study: NCT03308942," Jun. 18, 2018, retrieved on Oct. 26, 2020, retrieved from URL: https://clinicaltrials.gov/ct2/history/NCT03308942?V_5=View#StudyPageTop, 15 pages.
Anonymous, "Tesaro announces expansion to second stage of Jasper trial of Zejula in combination with TSR-042 in non-small cell lung cancer," Sep. 4, 2018, retrieved on Oct. 26, 2020, retrieved from URL: https://www.globenewswire.com/news-release/2018/09/04/1565255/0/en/TESARO-Announces-Expansion-to-Second-Stage-of-JASPER-Trial-of-ZEJULA-in-Combination-With-TSR-042-in-Non-Small-Cell-Lung-Cancer.html, 4 pages.
Baixeras et al., "Characterization of the lymphocyte activation gene 3-encoded protein. A new ligand for human leukocyte antigen class II antigens," J. Exp. Med., 1992, 176:327-337.
Bhatia et al., "Immunobiology of Merkel cell carcinoma: implications for immunotherapy of a polyomavirus-associated cancer," Curr. Oncol. Rep., 2011, 13(6):488-497.
Blackburn et al., "Coregulation of CD8+ T cell exhaustion by multiple inhibitory receptors during chronic viral infection," Nat. Immunol., 2009, 10:29-37.
Bois et al., "A phase I and pharmacokinetic study of novel taxane BMS-188797 and cisplatin in patients with advanced solid tumors," Br. J Cancer, 2006, 94(1):79-84.
Boland et al., "Microsatellite instability in colorectal cancer", Gastroenterology, 2010, 138(6):2073-2087.
Brinkman et al., "The making of bispecific antibodies," Mabs, 2017, 9(2):182-212.
ClinicalTrials.gov [online], "Niraparib in Combination With Pembrolizumab in Patients With Triple-negative Breast Cancer or Ovarian Cancer (Topacio)", Jan. 18, 2016, retrieved on Feb. 16, 2021, retrieved from URL <"https://clinicaltrials.gov/ct2/show/NCT02657889?term=NCT+02657889&draw=2&rank=1 ">, 10 pages.
Dann et al., "BRCA 1/2 mutations and expression: response to platinum chemotherapy in patients with advanced stage epithelial ovarian cancer," Gynecol. Oncol., 2012, 125(3):677-82.
Davies et al., "Antibody-antigen complexes," Annual Rev Biochem., 1990, 59:439-473.
De la Chapelle et al., "Clinical Relevance of Microsatellite Instability in Colorectal Cancer", Journal of Clinical Oncology, 2010, 28(20):3380-3387.
Domagala et al., "BRCA1/2-negative hereditary triple-negative breast cancers exhibit BRCAness : Hereditary triple-negative breast cancer and BRCAness", International Journal of Cancer, Apr. 2017, 140(7):1545-1550.
Dougherty et al., "Biological and clinical evidence for somatic mutations in BRCA1 and BRCA2 as predictive markers for olaparib response in high-grade serous ovarian cancers in the maintenance setting", Oncotarget, Jul. 2017, 8(27):43653-43661.
Du Bois et al., "Addition of Epimbicin as a Third Drug to Carboplatin-Paclitaxel in First-Line Treatment of Advanced Ovarian Cancer: A Prospectively Randomized Gynecologic Cancer Intergroup Trial by the Arbeitsgemeinschaft Gynaekologische Onkologie Ovarian Cancer Study Group and the Groupe d'Investigateurs Nationaux pour l'Etude des Cancers Ovariens", Journal of Clinical Oncology, Mar. 2006, 24(7):1127-1135.
Duggan et al., "Microsatellite Instability in Sporadic Endometrial Carcinoma", Journal of the National Cancer Institute, Aug. 1994, 86(16):1216-1221.
Dutcher et al., "A phase II study of interleukin-2 and lymphokine-activated killer cells in patients with metastatic malignant melanoma," J. Clin. Oncol., 1989, 7:477-485.
Erdal et al., "A prosurvival DNA damage-induced cytoplasmic interferon response is mediated by end resection factors and is limited by Trex1," Genes Dev. 2017, 31:353-369.
Foa et al., "Treatment of acute myeloid leukaemia patients with recombinant interleukin 2: a pilot study," Br. J. Haematol., 1991, 77:491-496.
Gadducci et al., "PARP inhibitors alone and in combination with other biological agents in homologous recombination deficient epithelial ovarian cancer: From the basic research to the clinic", Critical Reviews in Oncology/Hematology, Jun. 2017, 114:153-165.
Gelmon et al., "Olaparib in patients with recurrent high-grade serous or poorly differentiated ovarian carcinoma or triple-negative breast cancer: a phase 2, multicentre, open-label, non-randomized study," Lancet Oncol., 2011, 12:852-861.
Gill et al., "Combination of PARP Inhibitor with Temolozolamide Drive PARP1 Trapping and Apoptosis in Ewing's Sarcoma," PLOS One, 2015, 10(10):e0140988.
Goyal et al., "Hereditary cancer syndromes: utilizing DNA repair deficiency as therapeutic target", Familial Cancer, Feb. 2016, 15:359-366.
Grosso et al., "LAG-3 regulates CD8+ T cell accumulation and effector function in murine self- and tumor-tolerance systems," J. Clin. Invest., 2007, 117:3383-92.
Guo et al., "Combined TIM-3 blockade and CD137 activation affords the long-term protection in a murine model of ovarian cancer," Journal of Translational Medicine, 2013, 11:215.
Gurin et al., "Causes and Consequences of Microsatellite Instability in Endometrial Carcinoma", Molecular Biology and Genetics, Jan. 1999, 59(2):462-466.
Hamanishi et al., "Safety and Antitumor Activity of Anti-PD-1 Antibody, Nivolumab, in Patients With Platinum-Resistant Ovarian Cancer", Journal of Clinical Oncology, Sep. 2015, 33:4015-4022.
Hennessy et al., "Somatic Mutations in BRCA1 and BRCA2 Could Expand the Number of Patients That Benefit From Poly (ADP Ribose) Polymerase Inhibitors in Ovarian Cancer," J Clin Oncol. 2010, 28(22):3570-3576.
Heong et al., "Update on immune checkpoint inhibitors in gynecological cancers", Journal of Gynecological Oncology, Mar. 2017, 28(2):e20, 19 pages.
Higuchi et al., "CTLA-4 Blockade Synergizes Therapeutically with PARP Inhibition in BRCA1-Deficient Ovarian Cancer," Cancer Immunol Res., 2015, 3:1257-1268.

(56) References Cited

OTHER PUBLICATIONS

Huang et al., "Role of LAG-3 in regulatory T cells," Immunity, 2004, 21:503-513.
Huang et al., "The PARP1 inhibitor BMN 673 exhibits immunoregulatory effects in a Brca1(−/−) murine model of ovarian cancer," Biochem Biophys Res Commun., 2015, 463:551-556.
Huard et al., "Characterization of the major histocompatibility complex class II binding site on LAG-3 protein," Proc. Nail. Acad. Sci. USA, 1997, 94(11):5744-5749.
Huard et al., "Lymphocyte-activation gene 3/major histocompatibility complex class II interaction modulates the antigenic response of CD4+ T lymphocytes," Eur. J. Immunol., 1994, 24:3216-3221.
Huard et al., "T cell major histocompatibility complex class II molecules down-regulate CD4+ T cell clone responses following LAG-3 binding," Eur. J. Immunol., 1996, 26:1180-1186.
Javle et al., "The role of PARP in DNA repair and its therapeutic exploitation", British Journal of Cancer, Oct. 2011, 105(8):1114-1122.
Jiao et al., "PARP inhibitor upregulates PD-L1 expression and enhances cancer-associated immunosuppression," Clinical Cancer Research, 2017, 23(14):3711-3720.
Kelley et al., "Targeting DNA repair pathways for cancer treatment: what's new?," Future Oncol., 2014, 10(7):1215-37.
Kim et al., "PD-L1 expression on immune cells, but not on tumor cells, is a favorable prognostic factor for head and neck cancer patients," Sci. Rep., 2016, 6:36956.
Konstantinopoulos et al., "Dose-finding combination study of niraparib and pembrolizumab in patients (pts) with metastatic triple-negative breast cancer (TNBC) or recurrent platinum-resistant epithelial ovarian cancer (OC) (TOPACIO/Keynote-162)", Annals of Oncology, Sep. 2017, 28(5):V406-V407.
Konstantinopoulos et al., "Topacio: Preliminary activity and safety in patients (pts) with platinum-resistant ovarian cancer (PROC) in a phase 1/2 study of niraparib in combination with pembrolizumab", Gynecologic Oncology, Jun. 2018, 149(Suppl. 1):246.
Konstantinopoulos, "Pembrolizumab Plus Niraparib Shows Promise in Ovarian Cancer", SGO Annual Meeting, Mar. 27, 2018, retrieved on Feb. 16, 2021, retrieved from URL <"https://www.onclive.com/view/pembrolizumab-plus-niraparib-shows-promise-in-ovarian-cancer">, 3 pages.
Le et al., "PD-1 Blockade in Tumors with Mismatch-Repair Deficiency," N. Engl. J. Med., 2015, 372(26):2509-2520.
Ledermann et al., "Olaparib maintenance therapy in patients with platinum-sensitive relapsed serous ovarian cancer: a preplanned retrospective analysis of outcomes by BRCA status in a randomized phase 2 trial," The Lancet, 2014, 15(8):852-61.
Ledermann et al., "Olaparib Maintenance Therapy in Platinum-Sensitive Relapsed Ovarian Cancer," New England Journal of Medicine, 2012, 366:1382-92.
Lotze et al., "Interleukin 2," K.A. Smith, Academic Press, Inc., San Diego, Calif., 1988, 237.
Malmqvist, "Biospecific interaction analysis using biosensor technology," Nature, 1993, 361:186-187.
McCans, "Germline BRCA mutation testing to determine eligibility for olaparib maintenance therapy in women with platinum-sensitive relapsed ovarian cancer (including fallopian tube or primary peritoneal cancer) with high grade serous features or a high grade serous component. Applicant Submitted Proposed Protocol", MSAC Application 1380, Dec. 2014, 32 pages.
Mirza et al., "Niraparib Maintenance Therapy in Platinum-Sensitive Recurrent Ovarian Cancer," The New England Journal of Medicine, 2016, 375(22):2154-2164.
Moschetta et al., "BRCA somatic mutations and epigenetic BRCA modifications in serous ovarian cancer", Annals of Oncology, Aug. 2016, 27(8):1449-1455.
Mouw et al., "DNA Damage and Repair Biomarkers of Immunotherapy Response," Cancer Discov., 2017, 7:675-693.
Murali, "Classification of endometrial carcinoma: more than two types," Lancet Oncol., 2014, 15(7):e268-78.

Myers et al., "Optimal alignments in linear space", CABIOS, 1988, 4(1):11-17.
Ngiow et al., "Anti-TIM3 antibody promotes T cell IFN-γ-mediated antitumor immunity and suppresses established tumors," Cancer Res., 2011, 71:3540-3551.
Ngiow et al., "Prospects for TIM3-Targeted Antitumor Immunotherapy," Cancer Res., 2011, 71(21):6567-6571.
Nichino et al., "Developing a common language for tumor response to immunotherapy: immune-related response criteria using unidimensional measurements," Clin. Cancer Res., 2013, 19(14):3936-43.
Nomi et al., "Clinical significance and therapeutic potential of the programmed death-1 ligand/programmed death-1 pathway in human pancreatic cancer," Clin Cancer Res., 2007, 13:2151-2157.
PCT International Preliminary Report on Patentability dated Nov. 19, 2019 for PCT/US2018/033437, 12 pages.
PCT International Search Report and Written Opinion in International Appln. PCT/US2019/049346, dated Apr. 9, 2020, 19 pages.
PCT International Search Report dated Oct. 17, 2018 for PCT/US2018/033437, 6 pages.
PCT Invitation to Pay Additional Fees in International Appln. No. PCT/US2018/067653, dated Apr. 2, 2019, 18 pages.
Pearson, "Using the FASTA program to search protein and DNA sequence databases," Methods Mol. Biol., 1994, 24:307-331.
Pearson, "Using the FASTA program to search protein and DNA sequence databases," Methods Mol. Biol., 1994, 25:365-389.
Pfisterer et al., "Gemcitabine plus carboplatin compared with carboplatin in patients with platinum-sensitive recurrent ovarian cancer: an intergroup trial of the Ago-Ov AR, the NCIC CTG, and the EORTC GCG," J Clin. Oncol., 2006, 24(29):4699-707.
Popat et al., "Systematic Review of Microsatellite Instability and Colorectal Cancer Prognosis", Journal of Clinical Oncology, Jan. 2005, 23(3):609-618.
Popova et al., "Ploidy and large-scale genomic instability consistently identify basal-like breast carcinomas with BRCA1/2 inactivation," Cancer Res, 2012, 72:5454-62.
Rom-Jurek et al., "Regulation of Programmed Death Ligand 1 (PD-L1) Expression in Breast Cancer Cell Lines In Vitro and in Immunodeficient and Humanized Tumor Mice" Int. J. Mol. Sci., 2018, 16:563.
Rosenberg et al., "A progress report on the treatment of 157 patients with advanced cancer using lymphokine-activated killer cells and interleukin-2 or high-dose interleukin-2 alone," New England Journal of Medicine, 1987, 316(15):889-897.
Rosenberg et al., "The development of new immunotherapies for the treatment of cancer using interleukin-2. A review," Ann. Surgery, 1988, 208:121.
Sakuishi et al., "Targeting Tim-3 and PD-1 pathways to reverse T cell exhaustion and restore anti-tumor immunity," J. Exp. Med., 2010, 207:2187-2194.
Sandhu et al., "The poly(ADP-ribose) polymerase inhibitor niraparib (MK4827) in BRCA mutation carriers and patients with sporadic cancer: a phase 1 dose-escalation trial," Lancet Oncol, 2013, 14:882-892.
Sharma et al., "Primary, Adaptive, and Acquired Resistance to Cancer Immunotherapy," Cell, 2017, 168(4):707-723.
Shukuya et al., "Predictive Markers for the Efficacy of Anti-PD-1/PD-L1 Antibodies in Lung Cancer," Journal of Thoracic Oncology, 2016, 11(7):976-988.
Sierro et al., "The CD4-like molecule LAG-3, biology and therapeutic applications," Expert Opin. Ther. Targets., 2011, 15(1):91-101.
Smith, "Interleukin-2: inception, impact, and implications," Science, 1988, 240(4856):1169-1176.
Tentori et al., "Pharmacological Strategies to Increase the Antitumor Activity of Methylating Agents," Current Medicinal Chemistry, 2002, 9(13):1285-1301.
Turner et al., "Hallmarks of 'BRCAness' in sporadic cancers," Nat. Rev. Cancer, 2004, 4(10):814-19.
Udall et al., "PD-L1 diagnostic tests: a systematic literature review of scoring algorithms and test-validation metrics," Diagnostic Pathology, 2018, 13:12.

(56) References Cited

OTHER PUBLICATIONS

Umar et al., "Revised Bethesda Guidelines for Hereditary Nonpolyposis Colorectal Cancer (Lynch Syndrome) and Microsatellite Instability", Journal of the National Cancer Institute, Feb. 2004, 96(4):261-268.
Westrop et al., "Opportunities for immunotherapy in microsatellite instable colorectal cancer," Cancer Immunol. Immunother., 2016, 65(10):1249-1259.
Woo et al., "Immune inhibitory molecules LAG-3 and PD-1 synergistically regulate T-cell function to promote tumoral immune escape," Cancer Res., 2012, 72:917-927.
Woof et al., "Human antibody-Fc receptor interactions illuminated by crystal structures," Nat. Rev. Immunol., 2004, 4:89-99.
Workman et al., "Negative regulation of T cell homeostasis by lymphocyte activation gene-3 (CD223)," J. Immunol., 2005, 174:688-695.
Written Opinion of the International Searching Authority dated Oct. 17, 2018 for PCT/US2018/033437, 11 pages.
Zhu et al., "Programmed death-1 pathway blockade produces a synergistic antitumor effect: combined application in ovarian cancer", Journal of Gynecologic Oncology, Sep. 2017, 28(5):e64.
U.S. Appl. No. 62/356,461, filed Jun. 29, 2016, Hedley et al.
U.S. Appl. No. 62/402,427, filed Sep. 30, 2016, Hedley et al.
Ascierto et al., "Biomarkers for Immunostimulatory Monoclonal Antibodies in Combination Strategies for Melanoma and Other Tumor Types," Clin. Cancer. Res., 2013, 19(5):1009-1020.
Barber et al., "Restoring Function in Exhausted CD8 T Cells During Chronic Viral Infection," Nature, 2006, 439: 682-687.
Bennett et al., "Program death-1 Engagement Upon TCR Activation Has Distinct Effects on Costimulation and Cytokine-Driven Proliferation: Attenuation of ICOS, IL-4, and IL-21, but Not CD28, IL-7, and IL-15 Responses," J. Immunol., 2003, 170:711-8.
Berge et al., "Pharmaceutical Salts," J Pharmaceutical Sciences, 1977, 66(1):1-19.
Bertsias et al. "Genetic, Immunologic, and Immunohistochemical Analysis of the Programmed Death 1/programmed Death Ligand 1 Pathway in Human Systemic Lupus Erythematosus," Arthritis Rheum., 2009, 60(1):207-218.
Blank et al., "PD-L1/B7H-1 Inhibits the Effector Phase of Tumor Rejection by T Cell Receptor (TCR) Transgenic CD8+ T Cells," Cancer Res., 2004, 64(3):1140-1145.
Brown et al. "Blockade of Programmed death-1 Ligands on Dendritic Cells Enhances T Cell Activation and Cytokine Production," J. Immunol., 2003, 170(3):1257-1266.
Curtin, "Parp Inhibitors and Cancer Therapy," Lands Bioscience and Springer Bioscience, 2006: 218-233.
Dong et al., "Tumor-associated B7-H1 Promotes T-cell Apoptosis: A Potential Mechanism of Immune Evasion," Nat. Med., 2002, 8(8):793-800.
Eisenhauer et al., "New response evaluation criteria in solid tumors: Revised RECIST guideline (version 1.1.)," Eur. J. of Cancer, 2009, 45(2):228-247.
Flies et al., "Blockade of the B7-H1/PD-1 Pathway for Cancer Immunotherapy," Yale J. Biol. Med., 2011, 84(4):409-421.
Freeman et al., "Engagement of the PD-1 Immunoinhibitory Receptor by a Novel B7 Family Member Leads to Negative Regulation of Lymphocyte Activation," J. Exp. Med., 2000, 192(7): 1027-1034.
Greenwald et al., "The B7 Family Revisited," Annu. Rev. Immunol., 2000, 23:515-548.
Hamanishi et al., "Programmed Cell Death 1 Ligand 1 and Tumor-Infiltrating CD8+ T Lymphocytes are Prognostic Factors of Human Ovarian Cancer," Proc. Natl. Acad. Sci. USA, 2007, 104(9):3360-335.
Hirano et al., "Blockade of B7-H1 and PD-1 by Monoclonal Antibodies Potentiates Cancer Therapeutic Immunity," Cancer Res., 2005, 65(3):1089-1096.
Ishida et al., "Induced Expression of PD-1, a Novel Member of the Immunoglobulin Gene Superfamily, Upon Programmed Cell Death," Embo J., Jun. 10, 1992, 11(11):3887-95.

Iwai et al., "Involvement of PD-L1 on Tumor Cells in the Escape From Host Immune System and Tumor Immunotherapy by PD-L1 Blockade," Proc. Natl. Acad. Sci. USA, 2002, 99(9):12293-12297.
Iwai et al., "PD-1 Blockade Inhibits Hematogenous Spread of Poorly Immunogenic Tumor Cells by Enhanced Recruitment of Effector T Cells," Int. Immunol., 2005, 17(2):133-144.
Kroner et al., "A PD-1 Polymorphism Is Associated With Disease Progression in Multiple Sclerosis," Ann. Neurol., 2005, 58(1): 50-57.
Latchman et al., "PD-L2 Is a Second Ligand for PD-1 and Inhibits T Cell Activation," Nat. Immunol., 2001 2(3): 261-238.
Meyers et al., "Optimal Alignments in Linear Space," Comput. Appl. Biosci., 1989, 4(1):11-17.
Ni et al., "PD-1 Gene Haplotype Is Associated With the Development of Type 1 Diabetes Mellitus in Japanese Children," Hum. Genet., 2007, 121(2):223-232.
Nielsen et al., "Association of a Putative Regulatory Polymorphism in the PD-1 Gene With Susceptibility to Type 1 Diabetes," Tissue Antigens, 2003, 62(6):492-497.
Nishimura et al., "Development of Lupus-Like Autoimmune Diseases by Disruption of the PD-1 Gene Encoding an ITIM Motif-Carrying Immunoreceptor," Immunity, 1999, 11(2):141-1151.
Okazaki et al., "New Regulatory Co-Receptors: Inducible Co-Stimulator and PD-1," Curr. Opin. Immunol., 2002, 14(6):779-82.
Parry et al., "CTLA-4 and PD-1 Receptors Inhibit T-cell Activation by Distinct Mechanisms," Mol. Cell. Biol., 2005, 25(21):9543-9553.
Patnaik et al., "Phase I study of MK-3475 (anti-PD-1 monoclonal antibody) in patients with advanced solid tumors," Journal of Clinical Oncology, 2012, 30(15):Abstract #2512.
PCT International Search Report and Written Opinion in International Appln. No. PCT/US2018/054606, dated Mar. 28, 2019, 15 pages.
PCT International Search Report and Written Opinion in International Appln. No. PCT/US2018/053542, dated Dec. 14, 2 018, 8 pages.
PCT Invitation to Pay Additional Fees in International Appln. No. PCT/US2018/054606, dated Feb. 5, 2019, 10 pages.
Porichis et al., "Role of PD-1 in HIV Pathogenesis and as Target for Therapv," Curr. HIV/AIDS Rep., 2012, 9(1):81-90.
Rustin et al., "Definitions for Response and Progression in Ovarian Cancer Clinical Trials Incorporating RECIST 1.1 and CA 125 Agreed by the Gynecological Cancer Intergroup (GCIG)," Int J Gynecol Cancer, 2011, 21:419-423.
Sharpe et al., "The Function of Programmed Cell Death 1 and Its Ligands in Regulating Autoimmunity and Infection," Nat. Immunol., 2007, 8(3):239-245.
Tahoori et al., "Association of Programmed Cell death-1 (PDCD-1) Gene Polymorphisms With Rheumatoid Arthritis in Iranian Patients," Clin. Exp. Rheumatol., 2011, 29(5):763-767.
Tang et al., "Programmed Death 1 Pathway Inhibition in Metastatic Renal Cell Cancer and Prostate Cancer," Current Oncology Reports, 2013, 15(2):98-104.
Topalian et al., "Safety, Activity, and Immune Correlates of anti-PD-1 Antibody in Cancer," New England J. Med., 2012, 366(26):2443-2454.
Weber, "Immune Checkpoint Proteins: A New Therapeutic Paradigm for Cancer—Preclinical Background: CTLA-4 and PD-1 Blockade," Semin. Oncol., 2010, 37(5):430-4309.
Yamazaki et al., "Expression of Programmed Death 1 Ligands by Murine T Cells and APC," J. Immunol., 2002, 169(10):5538-5545.
Lee et al., "Safety and Clinical Activity of the Programmed Death-Ligand 1 Inhibitor Durvalumab in Combination With Poly (ADP-Ribose) Polymerase Inhibitor Olaparib or Vascular Endothelial Growth Factor Receptor 1-3 Inhibitor Cediranib in Women's Cancers: A Dose-Escalation, Phase I Study", Journal of Clinical Oncology, Jul. 2017, 35(19):2193-2202.
PCT International Preliminary Report on Patentability in International Application No. PCT/US2018/053542, dated Mar. 31, 2020, 5 pages.
PCT International Preliminary Report on Patentability in International Application No. PCT/US2018/054606, dated Apr. 8, 2020, 7 pages.

(56) References Cited

OTHER PUBLICATIONS

PCT International Preliminary Report on Patentability in International Application No. PCT/US2018/067653, dated Jun. 30, 2020, 11 pages.
PCT International Preliminary Report on Patentability in International Application No. PCT/US2019/049346, dated Mar. 9, 2021, 15 pages.
PCT International Search Report and Written Opinion in International Application No. PCT/US2018/067653, dated May 27, 2019, 18 pages.
American Cancer Society, Cancer Facts & Figures, 2018, 76 pages.
Anderson et al., "TIM-3 in autoimmunity," Current Opinion in Immunology, Dec. 2006, 18:665-669.
Anderson, "Tim-3, a negative regulator of anti-tumor immunity," Current Opinion in Immunology, Apr. 2012, 24(2):213-216.
Ayers et al., "IFN-γ-related mRNA profile predicts clinical response to PD-1 blockade," J. Clin. Invest., 2017, 127(8):2930-2940.
Bohnsack et al., "Adaptation of the immune-related response criteria: iRecist," ESMO, 2014, Abstract 4958.
Chiba et al., "Tumor-infiltrating DCs suppress nucleic acid-mediated innate immune responses through interactions between the receptor TIM-3 and the alarmin HMGB1," Nature Immunology, Jul. 2012, 13:832-842.
ClinicalTrials.gov [online], "A Study of Niraparib Combined With Bevacizumab Maintenance Treatment in Participants With Advanced Ovarian Cancer Following Response on Front-Line Platinum-Based Chemotherapy," U.S. National Library of Medicine, Oct. 31, 2017, retrieved on Mar. 18, 2022, retrieved from URL <https://clinicaltrials.gov/ct2/show/NCT03326193>, 13 pages.
ClinicalTrials.gov [online], "Niraparib in Combination With Cabozantinib (XL184) in Patients With Advanced Urothelial Cancer (Nicaragua) (Nicaragua)," U.S. National Library of Medicine, Feb. 7, 2018, retrieved on Mar. 18, 2022, retrieved from URL <https://clinicaltrials.gov/ct2/show/NCT03425201>, 12 pages.
ClinicalTrials.gov [online], "Niraparib Versus Niraparib-bevacizumab Combination in Women With Platinum-sensitive Epithelial Ovarian Cancer (Avanova)," U.S. National Library of Medicine, Feb. 3, 2015, retrieved on Mar. 18, 2022, retrieved from URL <https://clinicaltrials.gov/ct2/show/NCT02354131>, 10 pages.
ClinicalTrials.gov [online], "Platine, Avastin and OLAparib in 1st Line (PAOLA-1)," U.S. National Library of Medicine, Jun. 23, 2015, retrieved on Mar. 18, 2022, retrieved from URL <https://www.clinicaltrials.gov/ct2/show/NCT02477644>, 11 pages.
DeKruyff et al., "T Cell/Transmembrane, Ig, and Mucin-3 Allelic Variants Differentially Recognize Phosphatidylserine and Mediate Phagocytosis of Apoptotic Cells," The Journal of Immunology, Feb. 2010, 184(4):1918-1930.
Han et al., "Tim-3: an activation marker and activation limiter of innate immune cells," Frontiers in Immunology, Dec. 2013, 4(449):1-7.
Hao et al., "A new oral polybosphate adenosine ribose polymerase inhibitor—niraparib," Clinical Medication Journal, Jun. 2017, 15(6):13-17 (with English translation).
Hastings et al., "TIM-3 is Expressed on Activated Human CD4+ T Cells and Regulates Th1 and Th17 Cytokines," European Journal of Immunol., Oct. 2009, 39(9):2492-2501.
Huang et al., "CEACAM1 regulates TIM-3-mediated tolerance and exhaustion," Nature, 2014, 517(7534):386-390.
Huang et al., "CTLA4 blockade induces frequent tumor infiltration by activated lymphocytes regardless of clinical responses in humans," Clin. Can. Res., 2011, 17:4101-4109.
Jones et al., "Discovery of 2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and -2 Mutant Tumors," Journal of Medicinal Chemistry, Oct. 2009, 52(22):7170-7185.
Kane, "TIM Proteins and Immunity," Journal of Immunology, Mar. 2010, 184(6):2743-2749.
Killmurray, "Niraparib/Bevacizumab Combo Continues to Show Prolonged PFS in Patients With Advanced Ovarian Cancer," Targeted Oncology, Mar. 20, 2021, retrieved on Mar. 18, 2022, retrieved from URL <https://www.targetedonc.com/view/niraparib-bevacizumab-combo-continues-to-show-prolonged-pfs-in-patients-with-advanced-ovarian-cancer>, 3 pages.
Liberal et al., "The Impaired Immune Regulation of Autoimmune Hepatitis Is Linked to a Defective Galectin-9/Tim-3 Pathway," Hepatology, 2012, 56(2):677-686.
Miller et al., "The status of poly(adenosine diphosphate-ribose) polymerase (PARP) inhibitors in ovarian cancer, part 2: extending the scope beyond olaparib and BRCA1/2 mutations," Clinical Advances in Hematology & Oncology, 2016, 14(9):704-711.
Mirza et al., "Niraparib plus bevacizumab versus niraparib alone for platinum-sensitive recurrent ovarian cancer (NSGO-AVANOVA2/ENGOT-ov24): a randomised, phase 2, superiority trial," Lancet Oncology, Aug. 29, 2019, pp. 1-11.
Monney et al., "Th1-specific cell surface protein Tim-3 regulates macrophage activation and severity of an autoimmune disease," Nature, Jan. 2002, 415:536-541.
Nakayama et al., "Tim-3 mediates phagocytosis of apoptotic cells and cross-presentation," Blood, Apr. 2009, 113(16):3821-3830.
Qu, "Clinical analysis of 26 cases of ovarian cancer treated with bevacizumab," China Health Care & Nutrition, Dec. 2014, No. 4 (II): 1882 (with English translation).
Richter et al., "On the role of the inhibitory receptor LAG-3 in acute and chronic LCMV infection," International Immunology, Oct. 2009, 22(1):13-23.
Sakuishi et al., "Emerging Tim-3 functions in anti-microbial and tumor immunity," Trends in Immunology, Aug. 2011, 32(8):345-349.
Sameni et al., "Cabozantinib (XL184) inhibits growth and invasion of preclinical TNBC models," Clinical Cancer Research, Oct. 2015, 22(4): 923-934.
Schmid et al., "New perspectives in ovarian cancer treatment," Maturitas, Feb. 2014, 77(2):128-136.
Sternberg, "Niraparib-Bevacizumab Combo Improves Clinical Outcomes in Recurrent Ovarian Cancer," Cancer Network, Jun. 5, 2020, retrieved on Mar. 18, 2022, retrieved from URL <https://www.cancernetwork.com/view/niraparib-bevacizumab-combo-improves-clinical-outcomes-recurrent-ovarian-cancer>, 2 pages.
U.S. Food and Drug Administration, "Zejula (niraparib) capsules: Highlights of Prescribing Information," Mar. 2021, 37 pages.
Vergote et al., "A phase 2 randomised discontinuation trial of cabozantinib in patients with ovarian carcinoma," European Journal of Cancer, 2017, 83:229-236.
Wu et al., "Blockade of Tim-3 signaling restores the virus-specific CD8+ T-cell response in patients with chronic hepatitis B," European Journal of Immunology, 2012, 42(5):1180-1191.
Zhao et al., "A case of triple-negative breast cancer treated with bevacizumab," Journal of Practical Oncology, Jun. 2009, 24(3):291-292 (with English translation).
Zhu et al., "The Tim-3 ligand galectin-9 negatively regulates T helper type 1 immunity," Nature Immunology, 2005, 6:1245-1252.
Brown et al, "Combining DNA damaging therapeutics with immunotherapy: more haste, less speed", British Journal of Cancer, Nov. 9, 2017, 118 (3):312-324.
ClinicalTrials.gov [online], "A Phase I/II Study of MEDI4736 in Combination With Olaparib in Patients With Advanced Solid Tumors. (Mediola)," U.S. National Library of Medicine, Apr. 12, 2016, retrieved on Jul. 6, 2022, retrieved from URL<https://clinicaltrials.gov/ct2/show/NCT02734004>, 17 pages.
clinicaltrials.gov [online], "Phase I/II Study of the Anti-Programmed Death Ligand-1 Durvalumab Antibody (MEDI4736) in Combination With Olaparib and/or Cediranib for Advanced Solid Tumors and Advanced or Recurrent Ovarian, Triple Negative Breast, Lung, Prostate and Colorectal Cancer," NCT02484404, last updated on Nov. 1, 2022, retrieved on Nov. 9, 2022, retrieved from URL<https://www.clinicaltrials.gov/ct2/show/NCT02484404>, 15 pages.
Clinicaltrials.Gov, (2016). "NCT02657889: Niraparib in Combination With Pembrolizumab in Patients With Triple-negative Breast Cancer or Ovarian Cancer," Available online at <https://clinicaltrials.gov/ct2/show/NCT02657889>, 8 pages.
Extended European Search Report and Written Opinion dated Feb. 11, 2021, for EP Patent Application No. 18797986.9, 16 pages.

(56) References Cited

OTHER PUBLICATIONS

Hamanishi et al., "Immune Checkpoint Inhibition in Ovarian Cancer," International Immunology, Apr. 7, 2016, 28(7): 339-348.

Hamanishi et al., "PD1/PDL1 Blockade in Cancer Treatment: Perspectives and Issues," Int. J. Clin. Oncol., Feb. 22, 2016, 21: 462-473.

International Search Report and Written Opinion in International Appln. No. PCT/US2018/031876, dated Aug. 6, 2018, 14 pages.

Isnansetyo et al., "Cytotoxicity of Fucoidan from Three Tropical Brown Algae Against Breast and Colon Cancer Cell Lines," Pharmacogn J., 2017, 9(1):14-20.

Kuo et al., "Casuarinin from the Bark of *Terminalia aijuna* Induces Apoptosis and Cell Cycle Arrest in Human Breast Adenocarcinoma MCF-7 Cells," Planta Med., 2005, 71(3):237-243.

Liu et al, What is the Place of PARP Inhibitors in Ovarian Cancer Treatment?, Curr Oncol Rep, 2016, 18:29, 9 pages.

Mantovani et al., "The chemokine system in cancer biology and therapy," Science Direct, Feb. 2010, 21(1):27-39.

Mirza et al., "A phase I study of bevacizumab in combination with niraparib in patients with platinum-sensitive epithelial ovarian cancer: The ENGOT-OV24/AVANOVA1 trial," Journal of Clinical Oncology, May 20, 2016, 34(15_Suppl), 8 pages.

Morris et al, "A Comprehensive Clinical Guide" Cancer, 2005, Chapter 6, pp. 41-44.

Robillard et al., "Abstract 3650: Predinical evaluation of the PARP inhibitor rucaparib in combination with PD-1 and PD-L1 inhibition in a syngeneic BRCA1 mutant ovarian cancer model," Cancer Research, Jul. 1, 2017, 77(13_Supplement):3650.

Vela et al., "Chemokine receptor-specific antibodies in cancer immunotherapy: achievements and challenges," Frontiers in Immunology, Jan. 30, 2015, 6(12):1-15.

ClinicalTrials.gov [online], "Avelumab in Patients With MSS, MSI-H and POLE-mutated Recurrent or Persistent Endometrial Cancer and of Avelumab/Talazoparib and Avelumab/Axitinib in Patients With MSS Recurrent or Persistent Endometrial Cancer", U.S. National Library of Medicine, Sep. 23, 2016, retrieved on Aug. 17, 2021, retrieved from URL <"https://clinicaltrials.gov/ct2/show/NCT02912572">, 13 pages.

ClinicalTrials.gov [online], "History of Changes for Study: NCT02849496: Veliparib and Atezolizumab Either Alone or in Combination in Treating Patients With Stage III-IV Triple Negative Breast Cancer", U.S. National Library of Medicine, Sep. 12, 2016, retrieved on Aug. 17, 2021, retrieved from URL <"https://clinicaltrials.gov/ct2/history/NCT02849496?V_3=View#StudyPageTop">, 11 pages.

Crafton et al., "PARP inhibition and gynecologic malignancies: A review of current literature and on-going trials", Gynecologic Oncology, Jul. 2016, 142(3): 588-596.

Evans et al., "PARP inhibitors in ovarian cancer: evidence, experience and clinical potential" Therapeutic Advances in Medical Oncology, Feb. 2017, 9(4):253-267.

Landrum et al., "A phase I trial of pegylated liposomal doxorubicin (PLD), carboplatin, bevacizumab and veliparib in recurrent, platinum-sensitive ovarian, primary peritoneal, and fallopian tube cancer: An NRG Oncology/Gynecologic Oncology Group study", Gynecologic Oncology, Nov. 2015, 140(2):204-209.

Marchetti et al., "Olaparib, PARP1 inhibitor in ovarian cancer", Expert Opinion on Investigational Drugs, Jul. 2012, 21(10): 1575-1584.

McLachlan et al., "The current status of PARP inhibitors in ovarian cancer", Tumori: A Journal of Experimental and Clinical Oncology, Oct. 2016, 102(5): 433-444.

\* cited by examiner

MDA-MB-436
*BRCA1* mutant breast

SK6005
APC$^{Min/+}$ mutant skin

SEQUENCE LISTING

```
<160> NUMBER OF SEQ ID NOS: 19

<210> SEQ ID NO 1
<211> LENGTH: 117
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45
```

```
Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Pro Tyr Tyr Ala Met Asp Tyr Trp Gly Gln Gly Thr Thr Val
                100                 105                 110

Thr Val Ser Ser Ala
        115

<210> SEQ ID NO 2
<211> LENGTH: 108
<212> TYPE: PRT
<213> ORGANISM: Artificial Sequence
<220> FEATURE:
<223> OTHER INFORMATION: Synthetic Construct

<400> SEQUENCE: 2

Asp Ile Gln Leu Thr Gln Ser Pro Ser Phe Leu Ser Ala Tyr Val Gly
  1               5                  10                  15

Asp Arg Val Thr Ile Thr Cys Lys Ala Ser Gln Asp Val Gly Thr Ala
                 20                  25                  30

Val Ala Trp Tyr Gln Gln Lys Pro Gly Lys Ala Pro Lys Leu Leu Ile
             35                  40                  45

Tyr Trp Ala Ser Thr Leu His Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln His Tyr Ser Ser Tyr Pro Trp
                 85                  90                  95

Thr Phe Gly Gln Gly Thr Lys Leu Glu Ile Lys Arg
                100                 105

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Gly Phe Thr Phe Ser Ser Tyr Asp Met Ser
  1               5                  10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Thr Ile Ser Gly Gly Gly Ser Tyr Thr Tyr
  1               5                  10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct
```

<400> SEQUENCE: 5

Pro Tyr Tyr Ala Met Asp Tyr
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

Lys Ala Ser Gln Asp Val Gly Thr Ala Val Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Trp Ala Ser Thr Leu His Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Gln His Tyr Ser Ser Tyr Pro Trp Thr
1               5

<210> SEQ ID NO 9
<211> LENGTH: 443
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

```
Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 10
<211> LENGTH: 442
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45
```

Ser Thr Ile Ser Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Pro Tyr Tyr Ala Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 11
<211> LENGTH: 214
<212> TYPE: PRT

<213> ORGANISM: Artificial Sequence
<220> FEATURE:
<223> OTHER INFORMATION: Synthetic Construct

<400> SEQUENCE: 11

```
Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 12
<211> LENGTH: 116
<212> TYPE: PRT
<213> ORGANISM: Artificial Sequence
<220> FEATURE:
<223> OTHER INFORMATION: Synthetic Construct

<400> SEQUENCE: 12

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Gly Gly Ser Tyr Thr Tyr Tyr Gln Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Tyr Ala Met Asp Tyr Trp Gly Gln Gly Thr Thr Val
            100                 105                 110
```

Thr Val Ser Ser
        115

<210> SEQ ID NO 13
<211> LENGTH: 107
<212> TYPE: PRT
<213> ORGANISM: Artificial Sequence
<220> FEATURE:
<223> OTHER INFORMATION: Synthetic Construct

<400> SEQUENCE: 13

Asp Ile Gln Leu Thr Gln Ser Pro Ser Phe Leu Ser Ala Tyr Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Tyr Ser Ser Tyr Pro Trp
                85                  90                  95

Thr Phe Gly Gln Gly Thr Lys Leu Glu Ile Lys
            100                 105

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Gly Phe Thr Phe Ser Ser Tyr Asp
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Ile Ser Gly Gly Gly Ser Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Ala Ser Pro Tyr Tyr Ala Met Asp Tyr
1               5

<210> SEQ ID NO 17
<211> LENGTH: 6
<212> TYPE: PRT
<213> ORGANISM: Artificial Sequence
<220> FEATURE:

```
<223> OTHER INFORMATION: Synthetic Construct

<400> SEQUENCE: 17

Gln Asp Val Gly Thr Ala
1               5

<210> SEQ ID NO 18
<211> LENGTH: 3
<212> TYPE: PRT
<213> ORGANISM: Artificial Sequence
<220> FEATURE:
<223> OTHER INFORMATION: Synthetic Construct

<400> SEQUENCE: 18

Trp Ala Ser
1

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Gln His Tyr Ser Ser Tyr Pro Trp Thr
1               5
```

COMBINATION THERAPIES FOR TREATING CANCER WITH NIRAPARIB AND PD-1 INHIBITORS

CROSS REFERENCE TO RELATED APPLICATIONS

This application is a U.S. national stage application of PCT/2018/053542, filed internationally on Sep. 28, 2018 and claims the benefit of U.S. Provisional Application No. 62/566,398, filed Sep. 30, 2017, U.S. Provisional Application No. 62/578,298, filed Oct. 27, 2017, and U.S. Provisional Application No. 62/654,024, filed Apr. 6, 2018, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 757822000200SEQLIST.TXT, date recorded: Mar. 25, 2020, size: 16 KB).

BACKGROUND

Cancer is a serious public health problem, with about 595,690 people in the United States of America expected to die of cancer in 2016 alone according to the American Cancer Society, Cancer Facts & FIGS. 2016 (http://www.cancer.org/acs/groups/content/@research/documents/document/acspc-047079.pdf).

SUMMARY

The present disclosure encompasses the recognition that a combination therapy with an agent that inhibits programmed death-1 protein (PD-1) signaling and an agent that inhibits poly[ADP-ribose] polymerase (PARP) is useful for treating certain cancers. Among other things, the present disclosure provides the insight that combination therapy with both an agent that inhibits PD-1 signaling and an agent that inhibits PARP may reduce the effective dose of one or both agents.

In one aspect, the present disclosure provides a method of treating cancer in a subject, where the cancer is associated with one or more mutations in one or more of the following genes: Kras, PTEN, TP53, Apc, BRCA1, or BRCA2, and/or is associated with expression of LPA1, the method including administering a therapeutically effective amount of an agent that inhibits PARP ("anti-PARP therapy") and an agent that inhibits PD-1 signaling ("anti-PD-1 therapy") to a subject.

In another aspect, the present disclosure provides a method of treating cancer in a subject including the steps of: (a) determining whether a cancer cell in a sample from the subject has one or more mutations in one or more of the following genes: Kras, PTEN, TP53, Apc, BRCA1, or BRCA2, and/or determining whether a cancer cell in a sample from the subject expresses LPA1 at a level higher than a reference sample; and (b) administering a therapeutically effective amount of an agent that inhibits poly[ADP-ribose] polymerase (PARP) and an agent that inhibits programmed death-1 protein (PD-1) signaling to the subject if the cancer cell in the sample from the subject has one or more mutations in one or more of the following genes: Kras, PTEN, TP53, Apc, BRCA1, or BRCA2, and/or expresses LPA1 at a level higher than a reference sample.

In another aspect, the present disclosure provides a method of inducing or enhancing an immune response in a subject where the subject has a cancer that is associated with one or more mutations in one or more of the following genes: Kras, PTEN, TP53, Apc, BRCA1, or BRCA2, and/or associated with expression of LPA1, including administering a therapeutically effective amount of an agent that inhibits poly[ADP-ribose] polymerase (PARP) and an agent that inhibits programmed death-1 protein (PD-1) signaling to the subject.

In some embodiments, the subject is a human. In other embodiments, the subject is a non-human animal, for example, a mammal, including, for example, a dog, cat, horse, or cow.

Agents that inhibit PD-1 signaling include those that bind to and block PD-1 receptors on T cells without triggering inhibitory signal transduction, agents that bind to PD-1 ligands to prevent their binding to PD-1, agents that do both and agents that prevent expression of genes that encode either PD-1 or natural ligands of PD-1. In some embodiments, an agent that inhibits PD-1 signaling is an antibody agent. Anti-PD-1 antibody agents can include any polypeptide or polypeptide complex that includes immunoglobulin structural elements sufficient to confer specific binding. Exemplary antibody agents include, but are not limited to, monoclonal antibodies, polyclonal antibodies, antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody agent that inhibits PD-1 signaling is a monoclonal antibody or a derivative thereof. In some embodiments, an antibody agent that inhibits PD-1 signaling is a PD-1 antibody, a PD-L1 antibody, or a derivative thereof. PD-1 and PD-L1 antibodies include, for example, atezolizumab, avelumab, BGB-A317, BI 754091, CX-072, durvalumab, FAZ053, IBI308, INCSHR-1210, JNJ-63723283, JS-001, LY3300054, MEDI-0680, MGA-012, nivolumab, PD-L1 millamolecule, PDR001, pembrolizumab, PF-06801591, REGN-2810, TSR-042, any of the antibodies disclosed in WO2014/179664, and any derivatives thereof. In some certain embodiments, an agent includes combinations of agents that inhibit PD-1 signaling.

In some embodiments, an agent that inhibits PD-1 signaling is a small molecule, a nucleic acid, a polypeptide (e.g., an antibody), a carbohydrate, a lipid, a metal, or a toxin. In some embodiments, an agent that inhibits PD-1 signaling is an anti-PD-1 antibody agent. In some certain embodiments, an anti-PD-1 antibody agent is a surrogate anti-PD-1 antibody for administration to an animal subject (e.g., a murine antibody for administration to a mouse or rat). In some embodiments, an anti-PD-1 antibody agent is for administration to a human subject.

In some embodiments, an anti-PD-1 antibody agent is an antibody selected from the group consisting of: BGB-A317, BI 754091, IBI308, INCSHR-1210, JNJ-63723283, JS-001, MEDI-0680, MGA-012, nivolumab, PDR001, pembrolizumab, PF-06801591, REGN-2810, TSR-042 and derivatives thereof. In some embodiments, an anti-PD-1 antibody agent is pembrolizumab or a derivative thereof. In some embodiments, an anti-PD-1 antibody agent is nivomulab or a derivative thereof. In some embodiments, an anti-PD-1 antibody agent is TSR-042 or a derivative thereof. In some embodiments, the agent that inhibits PD-1 signaling is an anti-PD-1 antibody agent comprising a CDR-H1 sequence of GFTFSSYD (SEQ ID NO: 14), a CDR-H2 sequence of ISGGGSYT (SEQ ID NO: 15), a CDR-H3 sequence of ASPYYAMDY (SEQ ID NO: 16), a CDR-L1 sequence of QDVGTA (SEQ ID NO: 17), a CDR-L2 sequence of WAS (SEQ ID NO: 18), and a CDR-L3 sequence of QHYSSYPWT (SEQ ID NO: 19). In some embodiments, the agent that inhibits PD-1 signaling is an anti-PD-1 antibody agent comprising a heavy chain variable domain comprising the amino acid sequence of SEQ ID NO: 12 and a light chain variable domain comprising the amino acid sequence of SEQ ID NO: 13. In some embodiments, the agent that inhibits PD-1 signaling is an anti-PD-1 antibody agent comprising a heavy chain comprising the amino acid sequence of SEQ ID NO: 9 or SEQ ID NO: 10 and a light chain comprising the amino acid sequence of SEQ ID NO: 11.

In some embodiments, the agent that inhibits PD-1 signaling is an anti-PD-L1/L2 agent. In some embodiments, an anti-PD-L1/L2 agent is an anti-PD-L1 antibody agent. In some certain embodiments, an anti-PD-L1 antibody agent is a surrogate anti-PD-1 antibody for administration to an animal subject (e.g., a murine antibody for administration to a mouse or rat). In some embodiments, an anti-PD-L1 antibody agent is for administration to a human subject. In some embodiments, an anti-PD-L1 antibody agent is atezolizumab, avelumab, CX-072, durvalumab, FAZ053, LY3300054, PD-L1 millamolecule, or derivatives thereof.

In some embodiments, agents that inhibit PARP include agents that inhibit PARP-1 and/or PARP-2. In some embodiments, an agent that inhibits PARP is a small molecule, a nucleic acid, a polypeptide (e.g., an antibody), a carbohydrate, a lipid, a metal, or a toxin. In some embodiments, an agent that inhibits PARP is selected from the group consisting of: ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives of any of the preceding. In some embodiments, an agent that inhibits PARP is a small molecule. In some embodiments, an agent that inhibits PARP is an antibody agent. In some embodiments, an agent that inhibits PARP is a small molecule. In some embodiments, a small molecule agent that inhibits PARP is selected from the group consisting of: niraparib, olaparib, rucaparib, talazoparib, veliparib, and salts or derivatives thereof. In some embodiments, an agent that inhibits PARP is niraparib or a salt or derivative thereof. In some embodiments, an agent that inhibits PARP is a combination of agents.

In some embodiments, an agent that inhibits PD-1 signaling is administered to a subject who is receiving, has received or will receive treatment with niraparib, an orally active PARP inhibitor. In some certain embodiments, pembrolizumab, nivolumab, or TSR-042 is administered to a subject who is receiving, has received or will receive treatment with niraparib. In some certain embodiments, niraparib is administered to a subject who is receiving, has received or will receive treatment with pembrolizumab, nivolumab, or TSR-042.

In some embodiments, a subject of the present disclosure is BRCA positive. In other embodiments, the subject is BRCA negative. In some embodiments, the subject is gBRCA negative, tBRCA negative, or sBRCA negative. In some embodiments, the subject is tBRCA negative.

In some embodiments of the present disclosure, the cancer is associated with one or more mutations in at least two of the following genes: Kras, PTEN, TP53, Apc, BRCA1, or BRCA2, and/or is associated with expression of LPA1. In some embodiments, the cancer is associated with a mutation in Kras. In some embodiments where the cancer is associated with a mutation in Kras, the cancer is associated with at least one additional mutation selected from a mutation in PTEN or in TP53. In some embodiments, the cancer is associated with a mutation in Kras and a mutation in PTEN. In some embodiments, the cancer is associated with a mutation in Kras and a mutation in TP53. In some embodiments, the cancer is associated with a homozygous mutation in TP53. In other embodiments, the cancer is associated with a heterozygous mutation in TP53. In some embodiments, the cancer is associated with a homozygous mutation in PTEN. In other embodiments, the cancer is associated with a heterozygous mutation in PTEN.

In some embodiments, the cancer is associated with a Kras G12D mutation. In some embodiments, the cancer is associated with a PTEN−/− mutation. In some embodiments, the cancer is associated with a TP53−/− mutation. In some embodiments, the subject is BRCA negative and the cancer is associated with a Kras G12D mutation and a PTEN−/− mutation. In some embodiments, the subject is BRCA negative and the cancer is associated with a TP53−/− mutation. In some embodiments, the subject is BRCA negative and the cancer is associated with expression of LPA1. In some embodiments, the subject is BRCA positive and the cancer is associated with a Kras G12D mutation and a TP53−/− mutation. In some embodiments, the subject is BRCA positive and the cancer is associated with a BRCA1 mutation. In some embodiments, the subject is BRCA negative and the cancer is associated with a Apc$^{min/+}$ (heterozygous) mutation. In some embodiments, the cancer is associated with one or more mutations in one or more additional genes in addition to the one or more mutations in one or more of Kras, PTEN, TP53, Apc, BRCA1, or BRCA2.

In some embodiments, the agent that inhibits PD-1 signaling and the agent that inhibits PARP are administered according to a regimen that includes at least one 2-12 week treatment cycle. Treatment duration shall be determined by a medical practitioner. In embodiments, treatment may continue until disease progression or toxicity. In some embodiments a treatment cycle is at least 2 weeks, at least 3 weeks, at least 4 weeks, at least 5 weeks, at least 6 weeks, at least 7 weeks, or at least 8 weeks. In some embodiments, an anti-PD-1 therapy and an anti-PARP therapy are administered in repeating cycles of 21 days. In some embodiments, the agent that inhibits PD-1 signaling is administered on day one of cycle one. In some embodiments, the agent that inhibits PD-1 signaling is administered on day one of a subsequent cycle. In some embodiments, the agent that inhibits PD-1 signaling is administered between one to three days before or after day one of a subsequent cycle. In some embodiments, the regimen includes at least 3 treatment cycles.

In some embodiments, the agent that inhibits PD-1 signaling is administered at a dose that is equivalent to 200 mg pembrolizumab in a human subject or 2 mg/kg of pembrolizumab. In some embodiments, the agent that inhibits PD-1 signaling is administered intravenously. In related embodiments, the agent that inhibits PD-1 signaling is administered intravenously over about 30 minutes.

In some embodiments, an agent that inhibits PD-1 signaling is administered at a dose that is equivalent to 240 mg of nivolumab in a human subject or 3 mg/kg or. In some embodiments, an agent that inhibits PD-1 signaling is administered intravenously. In related embodiments, an agent that inhibits PD-1 signaling is administered intravenously over about 60 minutes.

In some embodiments where the agent that inhibits PD-1 signaling is an anti-PD-1 antibody agent, the anti-PD-1 antibody agent is administered at a dose of 1, 3 or 10 mg/kg. In some embodiments, the anti-PD-1 antibody agent is administered at a dose of 1, 3 or 10 mg/kg every two weeks. In some embodiments, the anti-PD-1 antibody agent is administered at a dose that is equivalent to 500 mg in a human subject. In some embodiments, the anti-PD-1 antibody agent is administered at a dose that is equivalent to 500 mg in a human subject every 3 weeks. In some embodiments, the anti-PD-1 antibody agent is administered at a dose that is equivalent to 1000 mg in a human subject. In some embodiments, the anti-PD-1 antibody agent is administered at a dose that is equivalent to 1000 mg in a human subject every 6 weeks. In some embodiments the anti-PD-1 antibody agent is administered at a dose that is equivalent to 500 mg in a human subject every 3 weeks for four doses followed by a dose of least one dose that is equivalent to 1000 mg in a human subject every six weeks. In some embodiments, the doses equivalent to 1000 mg are administered every six weeks after the first dose equivalent to 1000 mg until no further clinical benefit is achieved.

In some embodiments, an agent that inhibits PARP is administered at a reduced dose. In some embodiments, the reduced dose is less than a dose equivalent to the FDA-approved dose for niraparib for use as a monotherapy. In some embodiments, the reduced dose is less than a dose equivalent to the highest FDA-approved dose for niraparib for use as a monotherapy. In some embodiments, the reduced dose is less than the dose for niraparib for use as a monotherapy that has been approved by a regulatory agency other than the FDA. In some embodiments, the agent that inhibits PARP is administered at a dose that is equivalent to 200 mg of niraparib in a human subject once a day. In some embodiments, an agent that inhibits PARP is administered orally. In some embodiments, a dose of 100 mg or 200 mg of niraparib is administered once per day.

In some embodiments, a combination therapy includes treatment such that a subject receives an increased dose of an agent that inhibits PARP if the subject's hemoglobin ≥9 g/dL, platelets ≥100,000/μL and neutrophils ≥1500/μL for all labs performed during one or more cycles. In some embodiments, a dose of the agent that inhibits PARP is increased after two cycles. In some embodiments, the increased dose of the agent that inhibits PARP is for use as a single agent. In some embodiments, the increased dose of the agent that inhibits PARP is equivalent to 300 mg of niraparib in a human subject.

In some embodiments, the subject has previously been treated with one or more different cancer treatment modalities. In some embodiments, the subject has previously been treated with one or more of radiotherapy, chemotherapy or immunotherapy. In some embodiments, the subject has been treated with one, two, three, four, or five lines of prior therapy. In some embodiments, the subject has been treated with one line of prior therapy. In some embodiments, the subject has been treated with two lines of prior therapy. In some embodiments, a prior therapy is cytotoxic therapy. In some embodiments, the cytotoxic therapy includes chemotherapy.

In some embodiments of the present disclosure, the cancer is endometrial cancer, breast cancer, ovarian cancer, cervical cancer, fallopian tube cancer, testicular cancer, primary peritoneal cancer, colon cancer, colorectal cancer, small intestine cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, squamous cell carcinoma of the head and neck, prostate cancer, pancreatic cancer, mesothelioma, Merkel cell carcinoma, sarcoma, glioblastoma, and a hematological cancer, such as multiple myeloma, B-cell lymphoma, T-cell lymphoma, Hodgkin's lymphoma/primary mediastinal B-cell lymphoma, or chronic myelogenous leukemia.

DETAILED DESCRIPTION OF CERTAIN EMBODIMENTS

Definitions

Figure 1A:
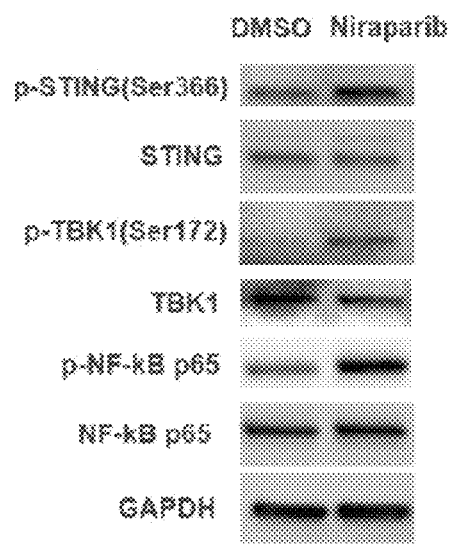
FIG. 1A depicts protein expression of Stimulator of Interferon Genes (STING), p-STING (Ser366), p-TBK1 (Ser172), TBK1, p-NF-κB p65, and NF-κB p65 in MDA-MB-436 cells upon 1 μm Niraparib treatment for 48 hours.

As used herein, the term "administration" typically refers to the administration of a composition to a subject or system. Those of ordinary skill in the art will be aware of a variety of routes that may, in appropriate circumstances, be utilized for administration to a subject, for example a subject (e.g., a human subject). For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

As used herein, the terms "dosage form" or "unit dosage form" refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a regimen that has been determined to correlate with a desired or beneficial outcome when administered to a relevant population (e.g., with a therapeutic regimen). Those of ordinary skill in the art appreciate that the total amount of a therapeutic composition or agent administered to a particular subject is determined by one or more attending physicians and may involve administration of multiple dosage forms.

As used herein, the term "regimen" refers to a set of unit doses (typically more than one) that are administered individually to a subject, typically separated by one or more periods of time. In some embodiments, a given therapeutic agent is administered according to a regimen, which may involve one or more doses. In some embodiments, a regimen comprises a plurality of doses each of which is separated in time from other doses. In some embodiments, individual doses are separated from one another by a time period of the same length; in some embodiments, a regimen comprises a plurality of doses, wherein the doses are separated by time periods of different length. In some embodiments, a regimen comprises doses of the same amount. In some embodiments, a regimen comprises doses of different amounts. In some embodiments, a regimen comprises at least one dose, wherein the dose comprises one unit dose of the therapeutic agent. In some embodiments, a regimen comprises at least one dose, wherein the dose comprises two or more unit doses of the therapeutic agent. For example, a dose of 250 mg can be administered as a single 250 mg unit dose or as two 125 mg unit doses. In some embodiments, a regimen is correlated with or result in a desired or beneficial outcome when administered across a relevant population (e.g., is a therapeutic regimen).

As used herein, the phrase "FDA-approved dose" refers to a dose or dosing regimen of an agent that has been determined by the U.S. Food & Drug Administration ("FDA") to have demonstrated sufficient safety and effectiveness to meet FDA's requirements for marketing approval. In some embodiments, safety and effectiveness of a dose or dosing regimen of an agent has been evaluated by conducting one or more clinical trials. In some embodiments, FDA marketing approval has been issued for an agent for one or more indications. In some certain embodiments, FDA marketing approval has been issued for an agent for treatment of a cancer.

As used herein, the term "patient", "subject", or "test subject" refers to any organism to which compound or compounds described herein are administered in accordance with the present invention, e.g., for experimental, diagnostic, prophylactic, and/or therapeutic purposes. Exemplary subjects include animals (e.g., mammals such as mice, rats, rabbits, canines, felines, horses, cattle, pigs, deer, non-human primates, and humans; insects; worms; birds; reptiles; amphibians; etc.). In some embodiments, a subject is a human. In some embodiments, a subject may be suffering from, and/or susceptible to a disease, disorder, and/or condition (e. g., cancer). In some embodiments, a patient is a human that has been diagnosed with a cancer. In some embodiments, a patient is a human possessing one or more female reproductive organs. In some embodiments, a patient is a human female (e.g., a woman) that has been diagnosed with a gynecological cancer or breast cancer (e.g., a cancer such as ovarian cancer, cancer of the fallopian tube(s), peritoneal cancer and breast cancer). As used herein, a "patient population" or "population of subjects" refers to a plurality of patients or subjects.

The term "sample", as used herein, refers to a composition that is obtained or derived from a subject (e.g., a human). Samples include sections of tissues such as biopsy and autopsy samples, and frozen sections taken for histologic purposes. The source of the tissue or cell sample may be solid tissue as from a fresh, frozen and/or preserved organ or tissue sample or biopsy or aspirate; blood or any blood constituents; bodily fluids. The tissue sample may also be primary or cultured cells or cell lines. Optionally, the tissue or cell sample is obtained from a disease tissue/organ. For example, a sample may contain cancer cells or is a cancer biopsy sample from a subject. The tissue sample may contain compounds which are not naturally intermixed with the tissue in nature such as preservatives, anticoagulants, buffers, fixatives, nutrients, antibiotics, or the like.

As used herein, a "therapeutically effective amount" refers to an amount of a therapeutic agent that produces the desired effect for which it is administered. In some embodiments, the term refers to an amount that is sufficient, when administered to a population suffering from or susceptible to a disease, disorder, and/or condition in accordance with a regimen, to treat the disease, disorder, and/or condition. In some embodiments, a therapeutically effective amount is one that reduces the incidence and/or severity of, and/or prevents or delays onset of, one or more symptoms of the disease, disorder, and/or condition. Those of ordinary skill in the art will appreciate that the term "therapeutically effective amount" does not in fact require for the disease, disorder, and/or condition to be resolved in a particular individual. Rather, a therapeutically effective amount may be an amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a regimen.

As used herein, "CA-125" means cancer antigen 125. A CA-125 test is used to measure the amount of the protein CA-125 in the blood of a patient. A CA-125 test may be used to monitor certain cancers during and after treatment, including use to evaluate prolongation of progression free survival. In some cases, a CA-125 test may be used to look for early signs of ovarian cancer in women with a very high risk of the disease.

As used herein, a "chemotherapeutic agent" refers to a chemical agent that inhibits the proliferation, growth, lifespan and/or metastatic activity of cancer cells. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines (e.g., altretamine, triethylenemelamine, trietylenephosphoramide, triethiylenethiophosphoramide and trimethylolomelamine); acetogenins; delta-9-tetrahydrocannabinol (e.g., dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (e.g., cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (e.g., T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; xeloda; ibandronate; topoisomerase inhibitor RFS 2000; difluoromethylornithine (DMFO); retinoids such as retinoic acid; capecitabine; pharmaceutically acceptable salts, acids or derivatives of any of the above; as well as combinations of two or more of the above such as CHOP, an abbreviation for a combined therapy of cyclophosphamide, doxorubicin, vincristine, and prednisone, and FOLFOX, an abbreviation for a treatment regimen with oxaliplatin (ELOXATIN™) combined with 5-FU and leucovovin.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGACE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOIECAN® topoisomerase 1 inhibitor; ABARELIX® rmRH; and pharmaceutically acceptable salts, acids or derivatives of any of the above.

A "antimetabolite chemotherapeutic agent" is an agent which is structurally similar to a metabolite, but cannot be used by the body in a productive manner. Many antimetabolite chemotherapeutic agents interfere with the production of the nucleic acids, RNA and DNA. Examples of antimetabolite chemotherapeutic agents include gemcitabine (GEMZAR®), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U®), dacarbazine (DTIC-DOMED), azocytosine, deoxycytosine, pyridmidene, fludarabine (FLUDARA®), cladrabine, 2-deoxy-D-glucose, etc. In some embodiments, an antimetabolite chemotherapeutic agent is gemcitabine. Gemcitabine HCl is sold by Eli Lilly under the trademark GEMZAR®.

As used herein, a "platinum-based chemotherapeutic agent" is a chemotherapeutic agent that comprises an organic compound which contains platinum as an integral part of the molecule. In some embodiments, a chemotherapeutic agent is a platinum agent. In some such embodiments, the platinum agent is selected from cisplatin, carboplatin, oxaliplatin, nedaplatin, triplatin tetranitrate, phenanthriplatin, picoplatin, or satraplatin.

As used herein, "BRCA mutation" or "mutation of BRCA" refers to a change or difference in the sequence of at least one copy of either or both of the BRCA1 or BRCA2 genes relative to an appropriate reference sequence (e.g., a wild type reference and/or a sequence that is present in non-cancerous cells in the subject). A mutation in the BRCA1/2 gene may result in a BRCA1/2 deficiency, which may include, for example a loss or reduction in the expression or function of the BRCA gene and/or encoded protein. Such mutations may also be referred to as "deleterious mutations" or may be suspected to be deleterious mutations. A BRCA mutation can be a "germline BRCA mutation," which indicates it was inherited from one or both parents. Germline mutations affect every cell in an organism and are passed on to offspring. A BRCA mutation can also be acquired during one's lifetime, i.e. spontaneously arising in any cell in the body ("soma") at any time during the patient's life, (e.g., non-inherited), which is referred to herein as a "sporadic BRCA mutation" or a "somatic BRCA mutation" interchangeably. Genetic tests are available, and known by those of skill in the art. For example, the BRACAnalysis CDx® kit is an in vitro diagnostic for detection and classification of germline BRCA1/2 variants. Using isolated genomic DNA, the BRACAnalysis CDx identifies mutations in the protein coding regions and intron/exon boundaries of the BRCA1 and BRCA2 genes. Single nucleotide variants and small insertions and deletions (indels) may be identified by polymerase chain reaction (PCR) and nucleotide sequencing. Large deletions and duplications in BRCA1 and BRCA2 may be detected using multiplex PCR. Indication of a "BRCA status" refers to, in at least some cases, whether a mutation is present in at least one copy of either BRCA1 or BRCA2. In some embodiments, indication of a BRCA status may refer to the mRNA expression level, methylation level or other epigenetic modification of either or both of BRCA1 and BRCA2. In some embodiments, a patient with a "positive BRCA status", "BRCA+", "BRCA-mutant" or "BRCA positive" refers to a patient from whom a sample has been determined to contain a mutation in BRCA1 and/or BRCA2. In some embodiments, a patient with a "positive BRCA status" refers to a patient from whom a sample has been determined to have a reduced expression of BRCA1 and/or BRCA2. In some embodiments, a patient with a "negative BRCA status", "BRCA-", "BRCA-wild type" or "BRCA negative" refers to a patient from whom a sample has been determined to have wildtype BRCA1 and/or BRCA2 sequence (e.g., $BRCA^{wt}$). In some embodiments, BRCA status is determined for the presence of germline BRCA mutations (e.g., $gBRCA^{mut}$). In some embodiments, BRCA status is determined for the presence of circulating tumor DNA BRCA mutations (e.g., $ctBRCA^{mut}$) and/or cell-free DNA BRCA mutations (e.g., $cfBRCA^{mut}$). In some embodiments, BRCA mutation status is performed on a blood sample of a subject. In some embodiments, BRCA status is determined for the presence of somatic BRCA mutations ($sBRCA^{mut}$) and/or tumor BRCA mutations ($tBRCA^{mut}$). In some embodiments, BRCA status is determined for the presence of one or more of $sBRCA^{mut}$, $tBRCA^{mut}$, $gBRCA^{mut}$ $ctBRCA^{mut}$, and $cfBRCA^{mut}$.

As used herein, the term "progression free survival" means the time period for which a subject having a disease (e.g. cancer) survives, without a significant worsening of the disease state. Progression free survival may be assessed as a period of time in which there is no progression of tumor growth and/or wherein the disease status of a patient is not determined to be a progressive disease. In some embodiments, progression free survival of a subject having cancer is assessed by evaluating tumor (lesion) size, tumor (lesion) number, and/or metastasis.

The term "progression" of tumor growth or a "progressive disease" (PD) as used herein in reference to cancer status indicates an increase in the sum of the diameters of the target lesions (tumors). In some embodiments, progression of tumor growth refers to at least a 20% increase in the sum of diameters of target lesions, taking as reference the smallest sum on study (this includes the baseline sum if that is the smallest on study). In some embodiments, in addition to a relative increase of 20%, the sum of diameters of target lesions must also demonstrate an absolute increase of at least 5 mm. An appearance of one or more new lesions may also be factored into the determination of progression of tumor growth. Progression for the purposes of determining progression free survival may also be determined if at least one of the following criteria is met: 1) tumor assessment by CT/MRI unequivocally shows progressive disease according to RECIST 1.1 criteria; or 2) additional diagnostic tests (e.g. histology/cytology, ultrasound techniques, endoscopy, positron emission tomography) identify new lesions or determine existing lesions qualify for unequivocal progressive disease AND CA-125-progression according to Gynecologic Cancer Intergroup (GCIG)-criteria (see Rustin et al., Int J Gynecol Cancer 2011; 21: 419-423 which is incorporated herein in its entirety); 3) definitive clinical signs and symptoms of PD unrelated to non-malignant or iatrogenic causes ([i] intractable cancer-related pain; [ii] malignant bowel obstruction/worsening dysfunction; or [iii] unequivocal symptomatic worsening of ascites or pleural effusion) AND CA-125-progression according to GCIG-criteria.

As used herein, the term "partial response" or "PR" refers to a decrease in tumor progression in a subject as indicated by a decrease in the sum of the diameters of the target lesions, taking as reference the baseline sum diameters. In some embodiments, PR refers to at least a 30% decrease in the sum of diameters or target lesions, taking as reference the baseline sum diameters. Exemplary methods for evaluating partial response are identified by RECIST guidelines. See E. A. Eisenhauer, et al., "New response evaluation criteria in solid tumors: Revised RECIST guideline (version 1.1.)," *Eur. J. of Cancer*, 45: 228-247 (2009).

As used herein, "stabilization" of tumor growth or a "stable disease" (SD) refers to nNeither sufficient shrinkage to qualify for PR nor sufficient increase to qualify for PD. In some embodiments, stabilization refers to a less than 30%, 25%, 20%, 15%, 10% or 5% change (increase or decrease) in the sum of the diameters of the target lesions, taking as reference the baseline sum diameters. Exemplary methods for evaluating stabilization of tumor growth or a stable disease are identified by RECIST guidelines. See E. A. Eisenhauer, et al., "New response evaluation criteria in solid tumors: Revised RECIST guideline (version 1.1.)," *Eur. J. of Cancer,* 45: 228-247 (2009).

As used herein, the term "complete response" or "CR" is used to mean the disappearance of all or substantially all target lesions. In some embodiments, CR refers to an 80%, 85%, 90%, 91%, 92%, 93%, 94%, 95%, 96%, 97%, 98%, 99% or 100% decrease in the sum of the diameters of the target lesions (i.e. loss of lesions), taking as reference the baseline sum diameters. In some embodiments, CR indicates that less than 10%, 9%, 8%, 7%, 6%, 5%, 4%, 3%, 2%, 1% or less of the total lesion diameter remains after treatment. Exemplary methods for evaluating complete response are identified by RECIST guidelines. See E. A. Eisenhauer, et al., "New response evaluation criteria in solid tumors: Revised RECIST guideline (version 1.1.)," *Eur. J. of Cancer,* 45: 228-247 (2009).

As used herein, a "hazard ratio" is the expression of the hazard or chance of events occurring in the treatment arm as a ratio of the events occurring in the control arm. Hazard ratios may be determined by any method known in the art, for example, the Cox model, a regression method for survival data, which provides an estimate of the hazard ratio and its confidence interval. The hazard ratio is an estimate of the ratio of the hazard rate in the treated versus the control group. The hazard rate is the probability that if the event in question has not already occurred, it will occur in the next time interval, divided by the length of that interval. An assumption of proportional hazards regression is that the hazard ratio is constant over time.

As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

As used herein, the term "polymorph" refers to a crystal structure of a compound. As used herein, the term "solvate" refers to a crystal form with either a stoichiometric or non-stoichiometric amount of solvent incorporated into the crystal structure. Similarly, the term "hydrate" refers to a crystal form with either a stoichiometric or non-stoichiometric amount of water incorporated into the crystal structure.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for oral administration, for example, drenches (aqueous or non-aqueous solutions or suspensions), tablets, e.g., those targeted for buccal, sublingual, and systemic absorption, boluses, powders, granules, pastes for application to the tongue. A pharmaceutical composition can also refer to a medicament.

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Those skilled in the art are well familiar with antibody structure and sequence elements, recognize "variable" and "constant" regions in provided sequences, and understand that there may be some flexibility in definition of a "boundary" between such domains such that different presentations of the same antibody chain sequence may, for example, indicate such a boundary at a location that is shifted one or a few residues relative to a different presentation of the same antibody chain sequence. Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload[e.g., a detectable moiety, a therapeutic moiety, a catalytic moiety, etc], or other pendant group [e.g., poly-ethylene glycol, etc.]

As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload[e.g., a detectable moiety, a therapeutic moiety, a catalytic moiety, etc], or other pendant group [e.g., poly-ethylene glycol, etc.]). In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution.

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

As used herein, the term "combination therapy" refers to a clinical intervention in which a subject is simultaneously exposed to two or more therapeutic regimens (e.g., two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

Cancers

Cancer is an abnormal growth of cells which tend to proliferate in an uncontrolled way and, in some cases, to metastasize (spread). Cancer is not one disease. It is a group of more than 100 different and distinctive diseases. Cancer can involve any tissue of the body and have many different forms in each body area. Most cancers are named for the type of cell or organ in which they start. A tumor can be cancerous or benign. A benign tumor means the tumor can grow but does not spread. A cancerous tumor is malignant, meaning it can grow and spread to other parts of the body. If a cancer spreads (metastasizes), the new tumor bears the same name as the original (primary) tumor. The frequency of a particular cancer may depend on gender. While skin cancer is the most common type of malignancy for both men and women, the second most common type in men is prostate cancer and in women, breast cancer.

The methods of the disclosure can be used to treat any type of cancer known in the art. Non-limiting examples of cancers to be treated by the methods of the present disclosure can include melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma, liver cancer, ovarian cancer, cervical cancer, thyroid cancer, glioblastoma, glioma, leukemia, lymphoma, mesothelioma, sarcoma and other neoplastic malignancies. Additionally, the invention includes refractory or recurrent malignancies whose growth may be inhibited using the methods of the invention. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, head and neck, tongue, larynx, and gullet), and adenocarcinoma (for example, prostate, small intestine, endometrium, cervical canal, large intestine, lung, pancreas, gullet, rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma.

In some embodiments, a patient or population of patients to be treated with combination therapy of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, mesothelioma, sarcoma or Merkel cell carcinoma. In some embodiments, a patient or population of patients to be treated with combination therapy of the present disclosure have a hematological cancer. In some embodiments, the patient has a hematological cancer such as Diffuse large B cell lymphoma ("DLBCL"), Hodgkin's lymphoma ("HL"), Non-Hodgkin's lymphoma ("NHL"), Follicular lymphoma ("FL"), acute myeloid leukemia ("AML"), or Multiple myeloma ("MM").

Gynecological Cancers

In some embodiments, the methods of the disclosure can be used to treat a gynecological cancer, such as ovarian cancer, fallopian tube cancer, or primary peritoneal cancer. In some embodiments, an ovarian cancer is an epithelial carcinoma. Epithelial carcinomas make up 85% to 90% of ovarian cancers. While historically considered to start on the surface of the ovary, new evidence suggests at least some ovarian cancer begins in special cells in a part of the fallopian tube. The fallopian tubes are small ducts that link a woman's ovaries to her uterus that are a part of a woman's reproductive system. In a normal female reproductive system, there are two fallopian tubes, one located on each side of the uterus. Cancer cells that begin in the fallopian tube may go to the surface of the ovary early on. The term 'ovarian cancer' is often used to describe epithelial cancers that begin in the ovary, in the fallopian tube, and from the lining of the abdominal cavity, call the peritoneum. In some embodiments, the cancer is or comprises a germ cell tumor. Germ cell tumors are a type of ovarian cancer develops in the egg-producing cells of the ovaries. In some embodiments, a cancer is or comprises a stromal tumor. Stromal tumors develop in the connective tissue cells that hold the ovaries together, which sometimes is the tissue that makes female hormones called estrogen. In some embodiments, a cancer is or comprises a granulosa cell tumor. Granulosa cell tumors may secrete estrogen resulting in unusual vaginal bleeding at the time of diagnosis.

In some embodiments, a gynecological cancer (e.g., ovarian cancer) is metastatic. In some embodiments, a gynecological cancer (e.g., ovarian cancer) is an advanced gynecological cancer (e.g., ovarian cancer). In some embodiments, a cancer is a stage II, stage III or stage IV gynecological cancer (e.g., ovarian cancer).

The expected incidence of epithelial ovarian cancer in women in the United States in 2012 is approximately 22,280 (15,500 deaths) and in Europe in 2012 was estimated at 65,538 patient cases (42,704 deaths). At diagnosis, most women present with advanced disease, which accounts for the high mortality rate. Standard therapy for advanced ovarian cancer typically consists of surgical debulking and a chemotherapy regimen. Initial chemotherapy consists of either taxane or platinum chemotherapy, or a combination thereof. While patients have been reported to respond initially to front line therapy, many of those patients who initially respond eventually relapse within 1 to 3 years. After relapse, patients respond moderately or poorly to subsequent chemotherapy. Additionally, intolerance to platinum agents is a clinical concern, as the risk of cumulative toxicities increases over the course of continued treatments. There is a significant unmet need due to the high recurrence rate, despite an initially high response rate. Attempts to improve the standard two-drug chemotherapy (carboplatin and paclitaxel) by adding a third cytotoxic drug (topotecan, gemcitabine, or doxil) have failed (du Bois et al, 2006 and Pfisterer et al, 2006).

Breast Cancer

In some embodiments, the methods of the disclosure can be used to treat breast cancer. Usually breast cancer either begins in the cells of the milk producing glands, known as the lobules, or in the ducts. Less commonly breast cancer can begin in the stromal tissues. These include the fatty and fibrous connective tissues of the breast. Over time the breast cancer cells can invade nearby tissues such the underarm lymph nodes or the lungs in a process known as metastasis. The stage of a breast cancer, the size of the tumor and its rate of growth are all factors which determine the type of treatment that is offered. Treatment options include surgery to remove the tumor, drug treatment which includes chemotherapy and hormonal therapy, radiation therapy and immunotherapy. The prognosis and survival rate varies widely; the five year relative survival rates vary from 98% to 23% depending on the type of breast cancer that occurs. Breast cancer is the second most common cancer in the world with approximately 1.7 million new cases in 2012 and the fifth most common cause of death from cancer, with approximately 521,000 deaths. Of these cases, approximately 15% are triple-negative, which do not express the estrogen receptor, progesterone receptor (PR) or HER2.

In some embodiments, a breast cancer is a metastatic breast cancer. In some embodiments, a breast cancer is an advanced breast cancer. In some embodiments, a cancer is a stage II, stage III or stage IV breast cancer. In some embodiments, a cancer is a stage IV breast cancer. In some embodiments, a breast cancer is a triple negative breast cancer.

Recurrent Cancers

In some embodiments, a patient has a recurrent cancer that has been previously treated with chemotherapy. In some embodiments, a chemotherapeutic agent is a platinum agent. In some such embodiments, the platinum agent is selected from cisplatin, carboplatin, oxaliplatin, nedaplatin, triplatin tetranitrate, phenanthriplatin, picoplatin, or satraplatin.

In some embodiments, a cancer is characterized as "platinum resistant." In some embodiments, a platinum resistant cancer is a cancer that has progressed within 3 years (e.g., within 30 months, within 24 months, within 18 months, within 12 months, within 6 months) after completing a platinum-based chemotherapy regimen. In some embodiments, a platinum resistant cancer is a cancer that has progressed while the patient is receiving platinum-based chemotherapy (i.e. the patient is "platinum refractory").

In some embodiments, a patient with a recurrent cancer who has been previously treated with platinum-based chemotherapy has experienced a response lasting at least 6 months (e.g., at least 6 months, 8 months, 10 months, 12 months, 14 months, 16 months, 18 months, 24 months) to platinum-based therapy. In some embodiments, a patient has experienced a response lasting at least 6 months to first-line platinum-based therapy but currently considered platinum-resistant. In some embodiments, a patient with a recurrent cancer has been treated with 1, 2, 3, 4, or 5 lines of prior chemotherapy. In some embodiments, a patient has a recurrent high-grade serous ovarian, fallopian tube, or primary peritoneal cancer and has been previously treated with chemotherapy for advanced/metastatic disease and has experienced a response lasting at least 6 months to first-line platinum-based therapy but currently considered platinum-resistant.

In some embodiments, a patient with cancer has received adjuvant therapy. In some embodiments, an adjuvant therapy is an additional cancer treatment that is given after a primary treatment to lower the risk that the cancer will come back. Adjuvant therapy may include chemotherapy, radiation therapy, hormone therapy, targeted therapy or biological therapy. In some embodiments, a patient with cancer has been treated with at least 1 prior regimen for advanced/metastatic disease has relapsed/progressed while on or within 1 month from completion of adjuvant chemotherapy. In some embodiments, a patient with a recurrent cancer has been treated with 1, 2, 3, 4, or 5 lines of prior chemotherapy. In some embodiments, a patient has a triple-negative breast cancer (TNBC) has been treated with at least 1 prior regimen for advanced/metastatic disease has relapsed/progressed while on or within 1 month from completion of adjuvant chemotherapy.

BRCA

In some embodiments, a cancer is characterized by deficiencies in DNA repair such as BRCA mutations. BRCA 1 and 2 were initially identified as tumor suppressor genes that were associated with increased incidence of certain malignancies when defective. In some embodiments, a cancer has one or more of germline BRCA mutation, sporadic BRCA mutation and BRCA promoter hypermethylation. In some embodiments, a cancer has a combination of two or more of germline BRCA mutation, sporadic BRCA mutation and BRCA promoter hypermethylation. Germline mutations of BRCA-1 and BRCA-2 genes are found in a majority of patients with an inherited breast or ovarian cancer. Inactivation of BRCA-1 or BRCA-2 gene by other mechanisms, including somatic BRCA-1/2 mutations and/or gene silencing by promoter hypermethylation, occurs in a significant portion of several sporadic cancers. In particular, for ovarian cancer, somatic BRCA-1 or BRCA-2 mutations are found in 10%-15% of all epithelial ovarian carcinomas (EOCs), and strongly reduced expression of BRCA-1 has been observed in a significant portion of sporadic ovarian cancers.

BRCA plays a key role in DNA repair, including homologous recombination. It is estimated that over half of high grade serous ovarian cancer suffered from defects in DNA repair. Tumor cells with BRCA deficiency may provide an opportunity for therapeutic intervention with agents that inhibit DNA repair pathways and exploit synthetic lethality mechanisms of cancer treatment.

In some embodiments, a subject to be treated by methods of the present disclosure is characterized by a "positive BRCA status", "BRCA+" or "BRCA-mutant." In some embodiments, a patient with a "positive BRCA status" refers to a patient from whom a sample has been determined to have a reduced expression of BRCA1 and/or BRCA2.

In some embodiments, a subject to be treated by methods of the present disclosure is characterized by a "negative BRCA status", "BRCA-" or "BRCA-wild type." In some embodiments a negative BRCA status refers to a patient from whom a sample has been determined to have wildtype BRCA1 and/or BRCA2 sequence (e.g., $BRCA^{wt}$).

Additional Mutations or Gene Overexpression Associated with Cancer

Various mutations of genes or overexpression of genes are associated with cancer. The present disclosure describes methods of treatment of cancer and methods of inducing or enhancing an immune response in a subject with cancer, where the cancer is associated with one or more mutations in one or more of the following genes: Kras, PTEN, TP53, Apc, BRCA1, or BRCA2, and/or is associated with expression of LPA1. In some embodiments, the cancer is associated with one or more mutations in additional genes. Mutations in any of these genes may be of any type, such as, for example, a point mutation, a deletion, or an insertion. Mutations may have a variety of effects such as reduced expression of a gene, loss of function of a protein encoded by the gene, or gain of function of a protein encoded by the gene. The mutation may be in one or both copies of the gene in a cancer cell. The presence of a mutation may be determined by any method known to one of skill in the art, such as, for example, isolating DNA from a cancer cell, sequencing relevant sections of the gene in question, and comparing to a reference sequence such as a wild type reference and/or a sequence that is present in non-cancerous cells in the subject. Where a cancer is associated with expression of a gene, such as LPA1, the expression of the gene is expressed at a higher level than a different cancer cell or a non-cancer cell.

Kras (Kirsten rat sarcoma viral oncogene homolog) is a proto-oncogene involved in cell signaling pathways that control cell growth, cell maturation, and cell death. Alterations of single nucleotides within the Kras gene and single amino acids in the encoded KRAS protein can result in activating mutations, which are linked to the development and progression of cancer. In particular, the Kras G12D mutation involves an amino acid substitution at position 12 from glycine to aspartic acid and is linked to several types of cancer, including bladder cancer, colorectal cancer, non-small cell lung cancer (NSCLC), ovarian cancer, and pancreatic cancer.

PTEN (phosphatase and tensin homolog) is a tumor suppressor gene that is mutated in a large number of cancers at high frequency. The protein encoded by PTEN is a phosphatidylinositol-3,4,5-trisphosphate 3-phosphatase, which negatively regulates the AKT/PKB cellular signaling pathways. Loss of function mutations and deletions of PTEN, such as PTEN−/−, inactivate the enzymatic activity of phosphatidylinositol-3,4,5-trisphosphate 3-phosphatase, leading to increased cell proliferation and reduced cell death. Inactivation of PTEN is associated with a variety of cancers, including lung cancer, breast cancer, prostate cancer, endometrial cancer, colon cancer, bladder cancer, and glioblastoma.

TP53 (tumor protein p53) is a tumor suppressor gene that encodes p53, a protein that contributes to genomic stability by binding to DNA and regulating gene expression to prevent mutations in the genome. TP53 is the frequently mutated in many human cancers, suggesting that TP53 plays a crucial role in preventing tumorigenesis. Loss of function mutations and deletions of TP53, such as TP53−/−, are associated with a majority of human cancers, including endometrial cancer, breast cancer, ovarian cancer, cervical cancer, fallopian tube cancer, testicular cancer, primary peritoneal cancer, colon cancer, colorectal cancer, small intestine cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, squamous cell carcinoma of the head and neck, prostate cancer, pancreatic cancer, mesothelioma, Merkel cell carcinoma, sarcoma, and a hematological cancer, such as multiple myeloma, B-cell lymphoma, T-cell lymphoma, Hodgkin's lymphoma/primary mediastinal B-cell lymphoma, and chronic myelogenous leukemia.

APC (Adenomatous polyposis *coli*), a tumor-suppressor gene belonging to the WNT signaling pathway, encodes the APC protein, which regulates transcription of cell proliferation genes via interaction with the β-catenin transcription factor. The binding of APC to β-catenin results in the ubiquitination and degradation of β-catenin and thus, suppression of WNT target genes. In contrast, loss of APC function enhances the transcription of β-catenin target genes, such as cyclin D and c-Myc, to promote cell proliferation. Germline and somatic mutations of APC are associated with a variety of cancers, such as colon cancer, colorectal cancer, small intestine cancer, squamous cell carcinoma of the head and neck, esophageal cancer, squamous cell carcinoma of the anogenital region, melanoma, testicular cancer, liver cancer, and lymphoma. In particular, humans with germline mutations of APC are predisposed to intestinal adenoma formation. In corresponding mouse models, Min (multiple intestinal neoplasia) is a mutant allele of APC and APC$^{Min}$ heterozygous mice are genetically predisposed to intestinal adenoma formation.

LPA1 (also known as LPAR1) is a proto-oncogene that encodes a lysophosphatidic acid (LPA) receptor, an integral membrane protein promoting cell survival, proliferation and migration. Aberrant and overexpression of LPA1 is implicated in a variety of cancers, including endometrial cancer, breast cancer, ovarian cancer, prostate cancer, lung cancer, colorectal cancer, bladder cancer, and melanoma.

Role of Poly(ADP-Ribose) Polymerases (PARPs)

Poly(ADP-ribose) polymerases (PARPs) are a family of enzymes that cleave NAD+, releasing nicotinamide, and successively add ADP-ribose units to form ADP-ribose polymers. Accordingly, activation of PARP enzymes can lead to depletion of cellular NAD+ levels (e.g., PARPs as NAD+ consumers) and mediates cellular signaling through ADP-ribosylation of downstream targets. PARP-1 is a zinc-finger DNA-binding enzyme that is activated by binding to DNA double or single strand breaks. It was known that anti-alkylating agents could deplete the NAD+ content of tumor cells, and the discovery of PARPs explained this phenomenon. (Parp Inhibitors and Cancer Therapy. Curtin N. in *Poly ADP Ribosylation*. ed. Alexander Burke, Lands Bioscience and Springer Bioscience, 2006: 218-233). Anti-alkylating agents induce DNA strand breaks, which activates PARP-1, which is part of the DNA repair pathway. Poly ADP-ribosylation of nuclear proteins by PARP-1 converts DNA damage into intracellular signals that can either activate DNA repair (e.g. by the base excision repair (BER) pathway); or trigger cell death in the presence of DNA damage that is too extensive and cannot be efficiently repaired.

PARP-2 contains a catalytic domain and is capable of catalyzing a poly(ADP-ribosyl)ation reaction. PARP-2 displays auto-modification properties similar to PARP-1. The protein is localized in the nucleus in vivo and may account for the residual poly(ADP-ribose) synthesis observed in PARP-1-deficient cells, treated with alkylating agents or hydrogen peroxide. Some agents that inhibit PARP (e.g., agents primarily aimed at inhibiting PARP-1) may also inhibit PARP-2 (e.g., niraparib).

The role of PARP enzymes in DNA damage response (e.g. repair of DNA in response to genotoxic stress) has led to the compelling suggestion that PARP inhibitors may be useful anti-cancer agents. PARP inhibitors may be particularly effective in treating cancers resulting from germ line or sporadic deficiency in the homologous recombination DNA repair pathway, such as BRCA-1 and/or BRCA-2 deficient cancers.

Pre-clinical ex vivo and in vivo experiments suggest that PARP inhibitors are selectively cytotoxic for tumors with homozygous inactivation of BRCA-1 and/or BRCA-2 genes, which are known to be important in the homologous recombination (HR) DNA repair pathway. The biological basis for the use of PARP inhibitors as single agents in cancers with defects in BRCA-1 and/or BRCA-2 is the requirement of PARP-1 and PARP-2 for base excision repair (BER) of the damaged DNA. Upon formation of single-strand DNA breaks, PARP-1 and PARP-2 bind at sites of lesions, become activated, and catalyze the addition of long polymers of ADP-ribose (PAR chains) on several proteins associated with chromatin, including histones, PARP itself, and various DNA repair proteins. This results in chromatin relaxation and fast recruitment of DNA repair factors that access and repair DNA breaks. Normal cells repair up to 10,000 DNA defects daily and single strand breaks are the most common form of DNA damage. Cells with defects in the BER pathway enter S phase with unrepaired single strand breaks. Pre-existing single strand breaks are converted to double strand breaks as the replication machinery passes through the break. Double strand breaks present during S phase are preferentially repaired by the error-free HR pathway. Cells with inactivation of genes required for HR, such as BRCA-1 and/or BRCA-2, accumulate stalled replication forks during S phase and may use error-prone non-homologous end joining (NHEJ) to repair damaged DNA. Both the inability to complete S phase (because of stalled replication forks) and error-prone repair by NHEJ, are thought to contribute to cell death.

Without wishing to be bound by theory, it is hypothesized that treatment with PARP inhibitors may selectively kill a subset of cancer cells with deficiencies in DNA repair pathways (e.g., inactivation of BRCA-1 and/or BRCA-2).

For example, a tumor arising in a patient with a germline BRCA mutation has a defective homologous recombination DNA repair pathway and would be increasingly dependent on BER, a pathway blocked by PARP inhibitors, for maintenance of genomic integrity. This concept of inducing death by use of PARP inhibitors to block one DNA repair pathway in tumors with pre-existing deficiencies in a complementary DNA repair pathways is called synthetic lethality.

The therapeutic potential of PARP inhibitors is further expanded by the observation that PARP inhibitors not only have monotherapy activity in HR-deficient tumors, but are also effective in preclinical models in combination with other agents such as cisplatin, carboplatin, alkylating and methylating agents, radiation therapy, and topoisomerase I inhibitors. In contrast to the rationale for monotherapy in which PARP inhibition alone is sufficient for cell death in HR-deficient cancers (due to endogenous DNA damage), PARP is required for repair of DNA damage induced by standard cytotoxic chemotherapy. In some cases, the specific role of PARP is not known, but PARP is known to be required to release trapped topoisomerase I/irinotecan complexes from DNA. Temozolomide-induced DNA damage is repaired by the BER pathway, which requires PARP to recruit repair proteins. Combination therapies that enhance or synergize the cancer therapy without significantly increasing toxicity would provide substantial benefit to cancer patients, including ovarian cancer patients.

PARP Inhibitors

Without wishing to be bound by theory, treatment with PARP inhibitors (e.g., PARP-1/2 inhibitors) may selectively kill a subset of cancer cell types by exploiting their deficiencies in DNA repair. Human cancers exhibit genomic instability and an increased mutation rate due to underlying defects in DNA repair. These deficiencies render cancer cells more dependent on the remaining DNA repair pathways and targeting these pathways is expected to have a much greater impact on the survival of the tumor cells than on normal cells.

In some embodiments, a PARP inhibitor is ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, including any salts or derivatives thereof. In some embodiments, an agent that inhibits PARP is a small molecule. In some embodiments, an agent that inhibits PARP is an antibody agent. In some embodiments, an agent that inhibits PARP is a combination of agents. In some certain embodiments, a PARP inhibitor is niraparib, olaparib, rucaparib, talazoparib, veliparib, or any combination thereof. In some embodiments, a PARP inhibitor can be prepared as a pharmaceutically acceptable salt. One of skill in the art will appreciate that such salt forms can exist as solvated or hydrated polymorphic forms.

Target engagement has also been demonstrated by measuring PARP activity in tumor homogenates from tumor xenograft studies. Niraparib has been shown to induce cell cycle arrest, particularly arrest in the G2/M phase of the cell cycle. Accordingly, in some embodiments, the present invention provides a method of inducing cell cycle arrest of a tumor cell, the method comprising administering niraparib to a patient in need thereof. In some embodiments, the present invention provides a method of inducing arrest of the G2/M phase of the cell cycle of a tumor cell, the method comprising administering niraparib to a patient in need thereof. In some embodiments, the present invention provides a method of inducing arrest in the G2/M phase of the cell cycle of BRCA-1 and/or BRCA-2-deficient cells, the method comprising administering niraparib to a patient in need thereof.

At diagnosis of ovarian cancer, most women present with advanced disease, which accounts for the high mortality rate. Patients with stage 2, 3 or 4 disease will undergo tumor reductive surgery if the disease is potentially resectable and may undergo subsequent chemotherapy for 4-8 cycles. Initial chemotherapy may consist of either IV chemotherapy or a combination of IV and intraperitoneal (IP) chemotherapy. IV chemotherapy usually consists of a taxane (paclitaxel or docetaxel) and a platinum (cisplatin or carboplatin). Approximately 75% of patients respond to front line therapy and are considered platinum sensitive, standardly defined as a minimum duration of 6 months following treatment with no relapse or disease progression. However, up to 70% of patients eventually relapse within 1 to 3 years. Attempts to improve the standard platinum based two-drug chemotherapy by adding a third cytotoxic drug have failed to affect either progression-free survival or overall survival and resulted in an increase in toxic effects (du Bois et al, 2006 and Pfisterer, 2006 et al). There is a high unmet need due to the high recurrence rate, even after an initially high response rate.

Niraparib

Niraparib, (3 S)-3-[4-{7-(aminocarbonyl)-2H-indazol-2-yl}phenyl]piperidine, is an orally available, potent, poly (adenosine diphosphate[ADP]-ribose) polymerase (PARP)-1 and -2 inhibitor. See WO 2008/084261 (published on Jul. 17, 2008) and WO 2009/087381 (published Jul. 16, 2009), the entirety of each of which is hereby incorporated by reference. Niraparib can be prepared according to Scheme 1 of WO 2008/084261. As used herein, the term "niraparib" means any of the free base compound ((3S)-3-[4-{7-(aminocarbonyl)-2H-indazol-2-yl}phenyl]piperidine), a salt form, including pharmaceutically acceptable salts, of (3S)-3-[4-{7-(aminocarbonyl)-2H-indazol-2-yl}phenyl]piperidine (e.g., (3 S)-3-[4-{7-(aminocarbonyl)-2H-indazol-2-yl}phenyl]piperidine tosylate), or a solvated or hydrated form thereof (e.g., (3S)-3-[4-{7-(aminocarbonyl)-2H-indazol-2-yl}phenyl]piperidine tosylate monohydrate). In some embodiments, such forms may be individually referred to as "niraparib free base", "niraparib tosylate" and "niraparib tosylate monohydrate", respectively. Unless otherwise specified, the term "niraparib" includes all forms of the compound (3S)-3-[4-{7-(aminocarbonyl)-2H-indazol-2-yl}phenyl]piperidine.

In some embodiments, niraparib can be prepared as a pharmaceutically acceptable salt. One of skill in the art will appreciate that such salt forms can exist as solvated or hydrated polymorphic forms. In some embodiments, niraparib is prepared in the form of a hydrate.

In certain embodiments, niraparib is prepared in the form of a tosylate salt. In some embodiments, niraparib is prepared in the form of a tosylate monohydrate.

The crystalline tosylate monohydrate salt of niraparib is being developed as a monotherapy agent for tumors with defects in the homologous recombination (HR) deoxyribonucleic acid (DNA) repair pathway and as a sensitizing agent in combination with cytotoxic agents and radiotherapy.

Niraparib is a potent and selective PARP-1 and PARP-2 inhibitor with inhibitory concentration at 50% of control ($IC_{50}$)=3.8 and 2.1 nM, respectively, and is at least 100-fold selective over other PARP-family members. Niraparib inhibits PARP activity, stimulated as a result of DNA damage caused by addition of hydrogen peroxide, in various cell lines with an $IC_{50}$ and an inhibitory concentration at 90% of control ($IC_{90}$) of about 4 and 50 nM, respectively.

Niraparib demonstrates selective anti-proliferative activity for cancer cell lines that have been silenced for BRCA-1 or BRCA-2, or carry BRCA-1 or BRCA-2 mutations compared to their wild type counterparts. The antiproliferative activity of niraparib on BRCA-defective cells is a consequence of a cell cycle arrest in G2/M followed by apoptosis. Niraparib is also selectively cytotoxic for selected Ewing's sarcoma, acute lymphocytic leukemia (ALL), non-small cell lung cancer (NSCLC), and small cell lung cancer (SCLC) cell lines, as well as for tumor cell lines carrying homozygous inactivation of the ATM gene. Niraparib demonstrates weak activity on normal human cells. In vivo studies demonstrated strong antitumor activity with BRCA-1 mutant breast cancer (MDA-MB-436), BRCA-2 mutant pancreatic cancer (CAPAN-1), ATM-mutant mantle cell lymphoma (GRANTA-519), serous ovarian cancer (OVCAR3), colorectal cancer (HT29 and DLD-1), patient derived Ewing's sarcoma, and TNBC xenograft models in mice.

Programmed Death 1 (PD-1)

Programmed Death 1 (PD-1) (also known as Programmed Cell Death 1) (encoded by the gene Pdcd1) is a type I transmembrane protein of 268 amino acids originally identified by subtractive hybridization of a mouse T cell line undergoing apoptosis (Ishida et al., *Embo J.*, 11: 3887-95 (1992)). The normal function of PD-1, expressed on the cell surface of activated T cells under healthy conditions, is to down-modulate unwanted or excessive immune responses, including autoimmune reactions.

PD-1 is a member of the CD28/CTLA-4 family of T-cell regulators, and is expressed on activated T-cells, B-cells, and myeloid lineage cells (Greenwald et al., *Annu. Rev. Immunol.*, 23: 515-548 (2005); and Sharpe et al., *Nat. Immunol.*, 8: 239-245 (2007)). PD-1 is an inhibitory member of the CD28 family of receptors that also includes CD28, CTLA-4, ICOS and BTLA. PD-1 is expressed on activated B cells, T cells, and myeloid cells (Agata et al., supra; Okazaki et al. (2002) *Curr. Opin. Immunol* 14:391779-82; Bennett et al. (2003) *J Immunol.* 170:711-8).

Two ligands for PD-1 have been identified, PD ligand 1 (PD-L1) and PD ligand 2 (PD-L2), both of which belong to the B7 protein superfamily (Greenwald et al, supra). PD-1 has been shown to negatively regulate antigen receptor signaling upon engagement of its ligands (PD-L1 and/or PD-L2).

PD-L1 is expressed in a variety of cell types, including cells of the lung, heart, thymus, spleen, and kidney (see, e.g., Freeman et al., *J. Exp. Med.*, 192(7): 1027-1034 (2000); and Yamazaki et al., *J. Immunol.*, 169(10): 5538-5545 (2002)). PD-L1 expression is upregulated on macrophages and dendritic cells (DCs) in response to lipopolysaccharide (LPS) and GM-CSF treatment, and on T-cells and B-cells upon signaling via T-cell and B-cell receptors. PD-L1 also is expressed in a variety of murine tumor cell lines (see, e.g., Iwai et al., *Proc. Nat.l Acad. Sci. USA*, 99(9): 12293-12297 (2002); and Blank et al., *Cancer Res.*, 64(3): 1140-1145 (2004)). In contrast, PD-L2 exhibits a more restricted expression pattern and is expressed primarily by antigen presenting cells (e.g., dendritic cells and macrophages), and some tumor cell lines (see, e.g., Latchman et al., *Nat.* *Immunol.*, 2(3): 261-238 (2001)). High PD-L1 expression in tumors, whether on the tumor cell, stroma, or other cells within the tumor microenvironment, correlates with poor clinical prognosis, presumably by inhibiting effector T cells and upregulating regulatory T cells (Treg) in the tumor.

PD-1 and family members are type I transmembrane glycoproteins containing an Ig variable-type (V-type) domain responsible for ligand binding and a cytoplasmic tail, which is responsible for the binding of signaling molecules. The cytoplasmic tail of PD-1 contains 2 tyrosine-based signaling motifs, an immunoreceptor tyrosine-based inhibition motif (ITIM) and an immunoreceptor tyrosine-based switch motif (ITSM). PD-1 negatively regulates T-cell activation, and this inhibitory function is linked to an ITSM in the cytoplasmic domain (see, e.g., Greenwald et al., supra; and Parry et al., *Mol. Cell. Biol.*, 25: 9543-9553 (2005)). Following T cell stimulation, PD-1 recruits the tyrosine phosphatases SHP-1 and SHP-2 to the ITSM motif within its cytoplasmic tail, leading to the dephosphorylation of effector molecules, such as CD3, PKC and ZAP70, which are involved in the CD3 T cell signaling cascade. The mechanism by which PD-1 down-modulates T cell responses is similar to, but distinct from, that of CTLA-4. PD-1 was shown to be expressed on activated lymphocytes, including peripheral CD4+ and CD8+ T cells, B cells, T regs, and natural killer cells. Expression has also been shown during thymic development on CD4−/CD8− (double-negative) T cells, as well as subsets of macrophages and dendritic cells. The ligands for PD-1 (PD-L1 and PD-L2) are constitutively expressed or can be induced in a variety of cell types. PD-L1 is expressed at low levels on various non-hematopoietic tissues, most notably on vascular endothelium, whereas PD-L2 protein is predominantly expressed on antigen-presenting cells found in lymphoid tissue or chronic inflammatory environments. Both ligands are type I transmembrane receptors containing both IgV- and IgC-like domains in the extracellular region and short cytoplasmic regions with no known signaling motifs. Binding of either PD-1 ligand to PD-1 inhibits T cell activation triggered through the T cell receptor. PD-L2 is thought to control immune T cell activation in lymphoid organs, whereas PD-L1 serves to dampen unwarranted T cell function in peripheral tissues. Although healthy organs express little (if any) PD-L1, a variety of cancers were demonstrated to express abundant levels of this T cell inhibitor, which, via its interaction with the PD-1 receptor on tumor-specific T cells, plays a critical role in immune evasion by tumors.

PD-1 deficiency can lead to autoimmunity. For example, C57BL/6 PD-1 knockout mice have been shown to develop a lupus-like syndrome (see, e.g., Nishimura et al., *Immunity*, 11: 141-1151 (1999)). In humans, a single nucleotide polymorphism in the PD-1 gene is associated with higher incidences of systemic lupus erythematosus, type 1 diabetes, rheumatoid arthritis, and progression of multiple sclerosis (see, e.g., Nielsen et al., *Tissue Antigens*, 62(6): 492-497 (2003); Bertsias et al., *Arthritis Rheum.*, 60(1): 207-218 (2009); Ni et al, *Hum. Genet.*, 121(2): 223-232 (2007); Tahoori et al., *Clin. Exp. Rheumatol.*, 29(5): 763-767 (2011); and Kroner et al., *Ann. Neural.*, 58(1): 50-57 (2005)). Abnormal PD-1 expression also has been implicated in T-cell dysfunctions in several pathologies, such as tumor immune evasion and chronic viral infections (see, e.g., Barber et al., *Nature*, 439: 682-687 (2006); and Sharpe et al., supra). PD-1 is abnormally expressed in a variety of cancers (see, e.g., Brown et al, *J. Immunol.*, 170: 1257-1266 (2003); and Flies et. al, Yale Journal of Biology and Medicine, 84:

409-421 (2011)), and PD-L1 expression in some renal cell carcinoma patients correlates with tumor aggressiveness.

Recent studies demonstrate that T-cell suppression induced by PD-1 also plays a role in the suppression of anti-tumor immunity. For example, PD-L1 is expressed on a variety of human and mouse tumors, and binding of PD-1 to PD-L1 on tumors results in T-cell suppression and tumor immune evasion and protection (Dong et al., *Nat. Med.,* 8: 793-800 (2002)). Expression of PD-L1 by tumor cells has been directly associated with their resistance to lysis by anti-tumor T-cells in vitro (Dong et al., supra; and Blank et al., *Cancer Res.,* 64: 1140-1145 (2004)). PD-1 knockout mice are resistant to tumor challenge (Iwai et al., *Int. Immunol.,* 17: 133-144 (2005)), and T-cells from PD-1 knockout mice are highly effective in tumor rejection when adoptively transferred to tumor-bearing mice (Blank et al., supra). Blocking PD-1 inhibitory signals using a monoclonal antibody can potentiate host anti-tumor immunity in mice (Iwai et al., supra; and Hirano et al., *Cancer Res.,* 65: 1089-1096 (2005)), and high levels of PD-L1 expression in tumors are associated with poor prognosis for many human cancer types (Hamanishi et al., *Proc. Natl. Acad. Sci. USA,* 104: 3360-335 (2007), Brown et al, *J. Immunol.,* 170: 1257-1266 (2003); and Flies et al., *Yale Journal of Biology and Medicine,* 84(4): 409-421 (2011)).

In view of the foregoing, strategies for inhibiting PD-1 activity to treat various types of cancer and for immunopotentiation (e.g., to treat infectious diseases) have been developed (see, e.g., Ascierto et al., *Clin. Cancer. Res.,* 19(5): 1009-1020 (2013)). In this respect, monoclonal antibodies targeting PD-1 have been developed for the treatment of cancer (see, e.g., Weber, *Semin. Oncol.,* 37(5): 430-4309 (2010); and Tang et al., *Current Oncology Reports,* 15(2): 98-104 (2013)). For example, nivolumab (also known as BMS-936558) produced complete or partial responses in non-small-cell lung cancer, melanoma, and renal-cell cancer in a Phase I clinical trial (see, e.g., Topalian, *New England J. Med.,* 366: 2443-2454 (2012)), and is currently in Phase III clinical trials. MK-3575 is a humanized monoclonal antibody directed against PD-1 that has shown evidence of antitumor activity in Phase I clinical trials (see, e.g., Patnaik et al., 2012 *American Society of Clinical Oncology (ASCO) Annual Meeting,* Abstract #2512). In addition, recent evidence suggests that therapies which target PD-1 may enhance immune responses against pathogens, such as HIV (see, e.g., Porichis et al., *Curr. HIV/AIDS Rep.,* 9(1): 81-90 (2012)). Despite these advances, however, there remains a need to develop effective therapies and regimens in humans.

Agents that Inhibit PD-1 Signaling

Agents that inhibit PD-1 signaling for use in combination therapies of the present disclosure include those that bind to and block PD-1 receptors on T cells without triggering inhibitory signal transduction, agents that bind to PD-1 ligands to prevent their binding to PD-1, agents that do both, and agents that prevent expression of genes that encode either PD-1 or natural ligands of PD-1. Compounds that bind to natural ligands of PD-1 include PD-1 itself, as well as active fragments of PD-1, and in the case of the B7-H1 ligand, B7.1 proteins and fragments. Such antagonists include proteins, antibodies, anti-sense molecules and small organics.

In some embodiments, an agent that inhibits PD-1 signaling binds to human PD-1. In some embodiments an agent that inhibits PD-1 signaling binds to human PD-L1.

In some embodiments, an agent that inhibits PD-1 signaling for use in combination therapies of the present disclosure is an antibody agent. In some embodiments, a PD-1 antibody agent binds an epitope of PD-1 which blocks the binding of PD-1 to any one or more of its putative ligands. In some embodiments, a PD-1 antibody agent binds an epitope of PD-1 which blocks the binding of PD-1 to two or more of its putative ligands. In some embodiments, a PD-1 antibody agent binds an epitope of a PD-1 protein which blocks the binding of PD-1 to PD-L1 and/or PD-L2. PD-1 antibody agents of the present disclosure may comprise a heavy chain constant region ($F_c$) of any suitable class. In some embodiments, a PD-1 antibody agent comprises a heavy chain constant region that is based upon wild-type IgG1, IgG2, or IgG4 antibodies, or variants thereof.

In some embodiments, an agent that inhibits PD-1 signaling is a monoclonal antibody, or a fragment thereof. In some embodiments, an antibody agent that inhibits PD-1 signaling is a PD-1 antibody or fragment thereof. Monoclonal antibodies that target PD-1 that have been tested in clinical studies and/or received marketing approval in the United. Examples of antibody agents that target PD-1 signaling include, for example, any of the antibody agents listed in the following Table 1:

TABLE 1

Antibody agents that target PD-1.

| Antibody Agent Target (Format) | Developer |
|---|---|
| Opdivo Nivolumab PD-1 (Human IgG4) | Bristol-Myers Squibb ONO |
| Keytruda Pembrolizumab PD-1 (Humanized IgG4) | Merck |
| Tecentriq Atezolizumab PD-L1 (Human IgG1) | Roche |
| Imfinzi Durvalumab PD-L1 (Human IgG1) | Astra Zeneca |
| Bavencio Avelumab PD-L1 (Human IgG1) | Merck KGaA/Pfizer |
| PDR001 PD-1 (Humanized IgG4) | Novartis |
| REGN2810 (SAR-439684) PD-1 (fully human IgG4) | Sanofi, Regeneron |
| BGB-A317 PD-1 (Humanized IgG4) engineered to not bind FcγRI | BeiGene |
| LY3300054 PD-L1 | Eli Lilly |
| BI 754091 (anti-PD-1) | Boehringer Ingelheim |
| IBI308 (anti-PD-1) | Innovent Biologics (Eli Lilly) |
| INCSHR-1210 (anti-PD-1) | Incyte |
| JNJ-63723283 (anti-PD-1) | Janssen Research & Development, LLC |
| JS-001 (anti-PD-1) | Shanghai Junshi Bioscience Co., Ltd. |
| MEDI0680 (AMP-514) anti-PD-1 (Humanized IgG4) | MedImmune Inc |
| MGA-012 (anti-PD-1) | MacroGenics |
| PF-06801591 (anti-PD-1) | Pfizer |
| REGN-2810 (anti-PD-1) | Regeneron |
| TSR-042 anti-PD-1 (Humanized IgG4) | TESARO |
| CX-072 anti-PD-L1 | CytomX Therapeutics |
| FAZ053 anti-PD-L1 | Novartis |
| PD-L1 millamolecule | Bristol-Myers Squibb |

In some embodiments, an antibody agent that inhibits PD-1 signaling is atezolizumab, avelumab, BGB-A317, BI 754091, CX-072, durvalumab, FAZ053, IBI308, INCSHR-1210, JNJ-63723283, JS-001, MEDI-0680, MGA-012, nivolumab, PDR001, pembrolizumab, PF-06801591, REGN-2810, TSR-042, or any of the antibodies disclosed in WO2014/179664. In some embodiments, an antibody agent that inhibits PD-1 signaling is a PD-1 antibody selected from the group consisting of BGB-A317, BI 754091, CX-072, FAZ053, IBI308, INCSHR-1210, JNJ-63723283, JS-001, LY3300054, MEDI-0680, MGA-012, nivolumab, PD-L1 millamolecule, PDR001, pembrolizumab, PF-06801591, REGN-2810, and TSR-042. In some embodiments, an antibody agent that inhibits PD-1 signaling is a PD-1 antibody selected from the group consisting of nivolumab, pembrolizumab, and TSR-042. In some embodiments, a PD-1 antibody is pembrolizumab. In some embodiments, a PD-1 antibody is nivolumab. In some embodiments, a PD-1 antibody is TSR-042.

Pembrolizumab is an anti-PD-1 monoclonal antibody ("mAb") (also known as MK-3475, SCH 9000475, Keytruda). Pembrolizumab is an immunoglobulin G4/kappa isotype humanized mAb. The mechanism of pembrolizumab consists of the mAb binding to the PD-1 receptor of lymphocytes to block the interaction of PD-1 with PD-L1 and PD-L2 ligands produced by other cells in the body, including tumor cells of certain cancers.

Similarly to pembrolizumab, nivolumab (also known as BMS-936558, Opdivo) was first approved by the FDA in 2014 to treat melanoma that cannot be surgically removed or has metastasized following treatment with ipilimumab and a BRAF inhibitor where appropriate.

In some embodiments, a PD-1 antibody agent is as disclosed in International Patent Application Publication WO2014/179664, the entirety of which is incorporated herein. In some embodiments, a PD-1 antibody agent comprises a heavy chain variable domain that is 90%, 95%, 97%, 98%, 99% or 100% identical to SEQ ID NO:1. In some embodiments, a PD-1 antibody agent comprises a light chain variable domain that is 90%, 95%, 97%, 98%, 99% or 100% identical to SEQ ID NO:2. In some embodiments, a PD-1 antibody agent comprises a heavy chain variable domain that is 90%, 95%, 97%, 98%, 99% or 100% identical to SEQ ID NO:1 and a light chain variable domain that is 90%, 95%, 97%, 98%, 99% or 100% identical to SEQ ID NO:2.

```
SEQ ID NO: 1 - PD-1 antibody agent heavy chain
variable domain
EVQLLESGGGLVQPGGSLRLSCAASGFTFSSYDMSWVRQAPGKGLEWVST

ISGGGSYTYYQDSVKGRFTISRDNSKNTLYLQMNSLRAEDTAVYYCASPY

YAMDYWGQGTTVTVSSA

SEQ ID NO: 2 - PD-1 antibody agent light chain
variable domain
DIQLTQSPSFLSAYVGDRVTITCKASQDVGTAVAWYQQKPGKAPKLLIYW

ASTLHTGVPSRFSGSGSGTEFTLTISSLQPEDFATYYCQHYSSYPWTFGQ

GTKLEIKR
```

In some embodiments, a PD-1 antibody agent comprises one or more CDR sequences as disclosed in International Patent Application Publication WO2014/179664, the entirety of which is incorporated herein. In some embodiments, a PD-1 antibody agent comprises one or more CDR sequences that is 90%, 95%, 97%, 98%, 99% or 100% identical to:

```
HC - CDR1    GFTFSSYDMS      SEQ ID NO: 3
HC - CDR2    TISGGGSYTY      SEQ ID NO: 4
HC - CDR3    PYYAMDY         SEQ ID NO: 5
LC - CDR1    KASQDVGTAVA     SEQ ID NO: 6
LC - CDR2    WASTLHT         SEQ ID NO: 7
LC - CDR3    QHYSSYPWT       SEQ ID NO: 8
```

In some embodiments, a PD-1 antibody agent comprises one, two or three heavy chain CDR sequences that is 90%, 95%, 97%, 98%, 99% or 100% identical to CDR sequences listed above. In some embodiments, a PD-1 antibody agent comprises one, two or three light chain CDR sequences that is 90%, 95%, 97%, 98%, 99% or 100% identical to CDR sequences listed above.

In some embodiments, a PD-1 antibody agent comprises a heavy chain that is 90%, 95%, 97%, 98%, 99% or 100% identical to SEQ ID NO:9, or a fragment thereof. In some embodiments, a PD-1 antibody agent comprises a heavy chain that is 90%, 95%, 97%, 98%, 99% or 100% identical to SEQ ID NO:10, or a fragment thereof. In some embodiments, a PD-1 antibody agent comprises a light chain that is 90%, 95%, 97%, 98%, 99% or 100% identical to SEQ ID NO:11, or a fragment thereof.

```
SEQ ID NO: 9 - heavy chain
EVQLLESGGGLVQPGGSLRLSCAASGFTFSSYDMSWVRQA PGKGLEWVS

TISGGGSYTYYQDSVKGRFTISRDNSKNTLYLQMNSLRAEDTAVYYCASP

YYAMDYWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPR EPQVYTLP

PSQEEMTKNQVSLTCLVKGFYPSDIAVEWESNGQPENNYKTT PPVLDSD

GSFFLYSRLTVDKSRWQEGNVFSCSVMHEALHNHYTQKSLSLS LGK

SEQ ID NO: 10 - heavy chain
EVQLLESGGGLVQPGGSLRLSCAASGFTFSSYDMSWVRQA PGKGLEWVS

TISGGGSYTYYQDSVKGRFTISRDNSKNTLYLQMNSLRAEDTAVYYCASP

YYAMDYWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPR EPQVYTLP

PSQEEMTKNQVSLTCLVKGFYPSDIAVEWESNGQPENNYKTT PPVLDSD

GSFFLYSRLTVDKSRWQEGNVFSCSVMHEALHNHYTQKSLSLS LG

SEQ ID NO: 11 - light chain
DIQLTQSPSFLSAYVGDRVTITCKASQDVGTAVAWYQQKPGKAPKLLIYW

ASTLHTGVPSRFSGSGSGTEFTLTISSLQPEDFATYYCQHYSSYPWTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

In some embodiments, a PD-1 antibody agent comprises a heavy chain variable domain that is 90%, 95%, 97%, 98%, 99% or 100% identical to SEQ ID NO:12, or a fragment thereof. In some embodiments, a PD-1 antibody agent comprises a light chain variable domain that is 90%, 95%, 97%, 98%, 99% or 100% identical to SEQ ID NO:13, or a fragment thereof. In some embodiments, a PD-1 antibody agent comprises a heavy chain variable domain that is 90%, 95%, 97%, 98%, 99% or 100% identical to SEQ ID NO:12 and a light chain variable domain that is 90%, 95%, 97%, 98%, 99% or 100% identical to SEQ ID NO:13.

```
SEQ ID NO: 12 - heavy chain variable domain
EVQLLESGGGLVQPGGSLRLSCAASGFTFSSYDMSWVRQAPGKGLEWVST

ISGGGSYTYYQDSVKGRFTISRDNSKNTLYLQMNSLRAEDTAVYYCASPY

YAMDYWGQGTTVTSS

SEQ ID NO: 13 - light chain variable domain
DIQLTQSPSFLSAYVGDRVTITCKASQDVGTAVAWYQQKPGKAPKLLIYW

ASTLHTGVPSRFSGSGSGTEFTLTISSLQPEDFATYYCQH YSSYPWTFG

QGTKLEIK
```

In some embodiments, a PD-1 antibody agent comprises one or more CDR sequences that is 90%, 95%, 97%, 98%, 99% or 100% identical to:

| | | | |
|---|---|---|---|
| HC - CDR1 | GFTFSSYD | SEQ ID NO: 14 |
| HC - CDR2 | ISGGGSYT | SEQ ID NO: 15 |
| HC - CDR3 | ASPYYAMDY | SEQ ID NO: 16 |
| LC - CDR1 | QDVGTA | SEQ ID NO: 17 |
| LC - CDR2 | WAS | SEQ ID NO: 18 |
| LC - CDR3 | QHYSSYPWT | SEQ ID NO: 19 |

In some embodiments, a PD-1 antibody agent comprises one, two or three heavy chain CDR sequences that is 90%, 95%, 97%, 98%, 99% or 100% identical to CDR sequences listed above. In some embodiments, a PD-1 antibody agent comprises one, two or three light chain CDR sequences that is 90%, 95%, 97%, 98%, 99% or 100% identical to CDR sequences listed above.

Assessing Therapeutic Response

Tumor response can be measured by, for example, the RECIST v 1.1 guidelines. The guidelines are provided by E. A. Eisenhauer, et al., "New response evaluation criteria in solid tumors: Revised RECIST guideline (version 1.1.)," *Eur. J. of Cancer*, 45: 228-247 (2009), which is incorporated by reference in its entirety. RECIST may be used as to assess one or more of tumor response to treatment, date of disease progression, and as a basis for all protocol guidelines related to disease status. RECIST guidelines require, first, estimation of the overall tumor burden at baseline, which is used as a comparator for subsequent measurements. In some embodiments, initial tumor imaging at the patient screening stage is performed within 21 days prior to the date of the first dose of study treatment. Tumors can be measured via use of any imaging system known in the art, for example, by a CT scan, or an X-ray. Magnetic resonance imaging (MRI) may be used, for example, when CT is contradicted or for imaging of the brain. In some embodiments, CT imaging is the imaging technique. In some embodiments, the same imaging technique is used for the patient throughout the entire study.

In some embodiments, measurable disease is defined by the presence of at least one measurable lesion. In some embodiments, when more than one measurable lesion is present at baseline, all lesions up to a maximum of five lesions total (and a maximum of two lesions per organ) representative of all involved organs should be identified as target lesions and will be recorded and measured at baseline (this means in instances where patients have only one or two organ sites involved a maximum of two and four lesions respectively will be recorded).

In some embodiments, target lesions are selected on the basis of their size (lesions with the longest diameter), to be representative of all involved organs, and/or selection for lesions that lend themselves to reproducible repeated measurements.

Lymph nodes may merit special mention since they are normal anatomical structures which may be visible by imaging even if not involved by tumor. Pathological nodes which are defined as measurable may be identified as target lesions have a short axis of >15 mm by CT scan. In some embodiments, only the short axis of these nodes contributes to the baseline sum. The short axis of the node is the diameter normally used by radiologists to judge if a node is involved by solid tumor. Nodal size is normally reported as two dimensions in the plane in which the image is obtained (for CT scan this is almost always the axial plane; for MRI the plane of acquisition may be axial, sagittal or coronal). The smaller of these measures is the short axis.

For example, an abdominal node which is reported as being 20 mm•30 mm has a short axis of 20 mm and qualifies as a malignant, measurable node. In this example, 20 mm should be recorded as the node measurement. All other pathological nodes (those with short axis >10 mm but <15 mm) should be considered non-target lesions. Nodes that have a short axis <10 mm are considered non-pathological and should not be recorded or followed.

A sum of the diameters (longest for non-nodal lesions, short axis for nodal lesions) for all target lesions will be calculated and reported as the baseline sum diameters. If lymph nodes are to be included in the sum, then as noted above, only the short axis is added into the sum. The baseline sum diameters will be used as reference to further characterize any objective tumor regression in the measurable dimension of the disease.

All other lesions (or sites of disease) including pathological lymph nodes should be identified as non-target lesions and should also be recorded at baseline. Measurements are not required and these lesions should be followed as 'present', 'absent', or in rare cases 'unequivocal progression.' In addition, it is possible to record multiple nontarget lesions involving the same organ as a single item on the case record form (e.g. 'multiple enlarged pelvic lymph nodes' or 'multiple liver metastases').

In some embodiments, the first on-study imaging assessment should be performed at 9 weeks (63 days±7 days) from the date of the first dose of the study treatment. In some embodiments, in the case of progressive disease (PD), a confirmatory image will be required 4 weeks later (91 days±7 days).

In some embodiments, subsequent imaging should be performed every 9 weeks (63 days±7 days) or more frequently if clinically indicated at the time of suspected disease progression.

In some embodiments, after 1 year of radiographic assessments, patients will have imaging performed every 12 weeks (84 days±7 days).

In some embodiments, imaging will continue to be performed until one of the following occurs: the start of a new cancer treatment, the patient withdrawals consent, the patient dies, or the end of the study has been reached.

In some embodiments, patients who discontinue study treatment for reasons other than PD, will continue post-treatment imaging studies for disease status follow-up every 9 weeks (63 days±7 days) depending on the length of treatment with the study until: disease progression, the patient starts a new treatment outside of the study, the patient withdrawals consent, the patient becomes lost to follow-up, the patient dies, or the end of the study has been reached.

In some embodiments, irRECIST guidelines will also be incorporated in cases of disease progression to account for unique tumor characteristics seen during treatment with pembrolizumab and to assess continuation of treatment in clinically stable patients until progression is confirmed. In some embodiments, RECIST v1.1 will be adapted to incorporate these special guidelines, as using RECIST v1.1 alone in immunotherapy trials would lead to the declaration of progressive disease (PD) too early. Antibody agents that inhibit PD-1 signaling (e.g., pembrolizumab) may produce antitumor effects by potentiating endogenous cancer-specific immune responses. The response patterns with this type of approach tend to extend beyond the typical time course of responses seen with cytotoxic agents and can manifest a clinical response after an initial increase in tumor burden or appearance of new lesions.

Therefore, in some embodiments if repeat imaging shows <20% increase in tumor burden compared with (1) nadir, stable, or improved previously indicated new lesion (if identified as cause for initial PD), and (2) stable/improved non-target disease (if identified as cause for initial PD), treatment may be continued or resumed, and the next imaging should be conducted according to the above protocol schedule of 9 weeks (63 days±7 days) or if it has been one year since beginning of treatment (first radiographic image taken), 12 weeks (84 days±7 days).

In some embodiments, incorporating both RECIST v1.1 plus irRESIST v1.1 guidelines, patients will be discontinued from the study if repeat imaging confirms PD due to any of the following: tumor burden remains ≥20% and at least a 5-mm absolute increase in tumor size compared with nadir, non-target disease resulting in initial PD is worse, new lesion resulting in initial PD is worse, additional new lesions appeared since last evaluation, additional new non-target progression is seen since last evaluation.

In some embodiments, incorporating both RECIST v1.1 plus irRESIST v1.1 guidelines, patients may remain on pembrolizumab while waiting for confirmation of PD if they are clinically stable, which means the patient has absence of signs and symptoms indicating clinically significant progression of disease including worsening of laboratory values, the patient has no decline in ECOG status (0=asymptomatic through 5=death), patient is absent of rapid progression of disease, and patient has absence of progressive tumor at critical anatomical sites. Patients on immunotherapy can have transient tumor flare in the first few months of treatment, but with subsequent disease response. Thus, it is best to keep patients on the treatment while waiting for confirmation of PD if possible.

In some embodiments, the primary efficacy endpoint for the study is objective response rate (ORR) defined as a proportion of patients achieving CR or PR as assessed by RECIST v1.1. ORR by irRESIST will also be evaluated as a secondary endpoint. Tumor assessments after the initiation of further anticancer therapy are excluded for assessment of best overall response.

In some embodiments, duration of response (DOR) will be evaluated as a secondary endpoint. In some embodiments, DOR is defined as the time from first documentation of CR or PR by RECIST v1.1 guidelines until (1) the time of first documentation of disease progression per RESIST v1.1 and (2) the time of first documentation of disease progression per irRESIST. In some embodiments, date of progression based on RESIST v1.1 or irRESIST may be overwritten in patients with OC if clinical criteria indicate earlier progression as adjucated by the study committee.

In some embodiments, disease control rate (DCR) will be assessed as a secondary endpoint and is defined as the proportion of patients achieving CR, PR, or SD as assessed by RESIST v1.1 and irRESIST.

In some embodiments, progression-free survival (PFS) will be assessed as secondary endpoint and is defined as the time from enrollment to the earlier date of assessment of progression or death by any cause in the absence of progression based on (1) the time of first documentation of disease progression per RESIST v1.1 and (2) the time of first documentation of disease progression per irRESIST. In some embodiments, date of progression based on RESIST v1.1 or irRESIST may be overwritten in patients with OC if clinical criteria indicate earlier progression as adjucated by the study committee.

In some embodiments, overall survival (OS) will be assessed as a secondary endpoint and is defined as the time from date of first dose of study treatment to the date of death by any cause. New malignancy information will also be collected as part of this assessment.

In some embodiments, tumor markers (CA-125) will not be used for defining objective responses or disease progression, but can be used for clinical decisions.

In some embodiments, clinical criteria GCIG will be used for management of OC patients with clinical events (e.g., niraparib bowel obstruction) without radiographic evidence of disease progression.

In some embodiments, the present disclosure includes comparisons of results achieved for two or more agents, entities, situations, sets of conditions, populations etc. As will be understood by those of skill in the art, such agents, entities, situations, sets of conditions, populations, etc. can be considered "comparable" to one another when they are not identical but are sufficiently similar to permit comparison therebetween so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Comparisons as described herein are often made to an appropriate "reference". As used herein, the term "reference" refers to a standard or control relative to which a comparison is performed. For example, in some embodiments, an agent, animal, individual, population, sample, sequence, or value of interest is compared with a reference or control agent, animal, individual, population, sample, sequence, or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Pharmacokinetics

In some embodiments patients may be evaluated for pharmacokinetics information. Pharmacokinetic data can provide insight regarding the fate of a given drug (e.g., therapeutic agent) from administration to elimination from the human body.

Pharmacokinetic data can be obtained by known techniques in the art. Due to the inherent variation in pharmacokinetic and pharmacodynamic parameters of drug metabolism in human subjects, appropriate pharmacokinetic and pharmacodynamic profile components describing a particular composition can vary. Typically, pharmacokinetic and pharmacodynamic profiles are based on the determination of the mean parameters of a group of subjects. The group of subjects includes any reasonable number of subjects suitable for determining a representative mean, for example, 5 subjects, 10 subjects, 16 subjects, 20 subjects, 25 subjects, 30 subjects, 35 subjects, or more. The mean is determined by calculating the average of all subject's measurements for each parameter measured.

In some embodiments, a patient population includes one or more subjects ("a population of subjects") suffering from metastatic disease.

In some embodiments, a patient population includes one or more subjects that is suffering from or susceptible to cancer. In some embodiments, a patient population includes one or more subjects (e.g., comprises or consists of subjects) suffering from cancer. For example, in some embodiments, a patient population suffering from cancer may have previously been treated with a prior therapy, for example, radiation and/or chemotherapy.

In some embodiments, the pharmacokinetic parameter(s) can be any parameters suitable for describing the present composition.

General Protocol for Dosing

As described herein, provided methods comprise administering a therapy that inhibits PARP and a therapy that inhibits PD-1 signaling a in combination to a patient, a subject, or a population of subjects according to a regimen that achieves any one of or combination of: prolonged progression free survival; reduced hazard ratio for disease progression or death; and/or prolonged overall survival or a positive overall response rate.

In some embodiments, an agent that inhibits PARP (e.g., niraparib) is administered in combination (e.g., simultaneously or sequentially) with an agent that inhibits PD-1 signaling. In some embodiments, an agent that inhibits PD-1 signaling is a protein, antibody, anti-sense molecule or small organic molecule inhibitor of PD-1 signaling. In some embodiments, an agent that inhibits PD-1 signaling binds to PD-1. In some embodiments, an agent that inhibits PD-1 signaling is an anti-PD-1 or an anti-PD-L1 antibody agent.

In some embodiments, an agent that inhibits PARP (e.g., niraparib) is administered in combination (e.g., simultaneously or sequentially) with an immunotherapy (e.g. a PD-1 antibody agent). In some embodiments, the immunotherapy is or comprises administration of an agent that targets a specific antigen (e.g. PD-1); in some embodiments, immunotherapy is or comprises administration of an antibody agent that targets PD-1 or PD-L1 (e.g., an anti-PD-1 or an anti-PD-L1 antibody agent).

In some embodiments, one or more doses of an agent that inhibits PARP (e.g., niraparib) is administered before, during, or after administration of one or more doses of an agent that inhibits PD-1 signaling (e.g., an anti-PD-1 or an anti-PD-L1 antibody agent). In some embodiments, an agent that inhibits PARP (e.g., niraparib) and an agent that inhibits PD-1 signaling (e.g., an anti-PD-1 or an anti-PD-L1 antibody agent) are administered in overlapping regimens. In some embodiments, at least one cycle of an agent that inhibits PARP (e.g., niraparib) is administered prior to initiation of therapy with an agent that inhibits PD-1 signaling (e.g., an anti-PD-1 or an anti-PD-L1 antibody agent). In some embodiments, administration "in combination" includes administration of an agent that inhibits PARP (e.g., niraparib) and simultaneously or sequentially administering an agent that inhibits PD-1 signaling (e.g., an anti-PD-1 or an anti-PD-L1 antibody agent.

In some embodiments, administration of a particular dose or cycle of an agent that inhibits PARP (e.g., niraparib) is separated in time from a particular dose or cycle of an agent that inhibits PD-1 signaling (e.g., an anti-PD-1 or an anti-PD-L1 antibody agent) by a time period having a length that may be, for example, 1 minute, 5 minutes, 30 minutes, 1 hour, 2 hours, 5 hours, 10 hours, 12 hours, 24 hours, 48 hours, 72 hours, 96 hours, 1 week, 2 weeks, or more. In some embodiments, the range may be bounded by a lower limit and an upper limit, the upper limit being larger than the lower limit. In some embodiments, the lower limit may be about 1 minute, about 5 minutes, about 15 minutes, about 30 minutes, about 45 minutes, about 1 hour, about 2 hours, about 4 hours, about 6 hours, about 12 hours, about 24 hours, about 48, hours, about 72 hours, about 96 hours, or about 1 week. In some embodiments, the upper limit may be about 2 weeks, about 3 weeks, about 4 weeks, about 5 weeks, about 6 weeks, about 8 weeks, or about 12 weeks. In some embodiments, the administration of a particular dose of an agent that inhibits PARP (e.g., niraparib) is separated in time from a particular dose of an agent that inhibits PD-1 signaling (e.g., an anti-PD-1 or an anti-PD-L1 antibody agent) by a time period within the range of about 1 minute to about 12 weeks. In some embodiments, the range may be about 1 minute to about 8 weeks. In some embodiments, the range may be about 1 minute to about 6 weeks. In some embodiments, the range may be about 1 minute to about 4 weeks. In some embodiments, the range may be about 1 minute to about 2 weeks. In some embodiments, the range may be about 1 minute to about 1 week. In some embodiments, the range may be about 1 minute to about 96 hours. In some embodiments, the range may be about 1 minute to about 72 hours. In some embodiments, the range may be about 1 minute to about 48 hours. In some embodiments, the range may be about 1 minute to about 24 hours. In some embodiments, the range may be about 1 minute to about 12 hours. In some embodiments, the range may be about 1 minute to about 8 hours. In some embodiments, the range may be about 1 minute to about 4 hours. In some embodiments, the range may be about 1 minute to about 2 hours. In some embodiments, the range may be about 1 minute to about 1 hour. In some embodiments, the range may be about 1 minute to about 11 minute.

In some embodiments, combination therapy with an agent that inhibits PARP (e.g., niraparib) and an agent that inhibits PD-1 signaling (e.g., an anti-PD-1 or an anti-PD-L1 antibody agent) is administered to a patient or population of subjects who has exhibited response to prior therapy. In some embodiments, the patient or population of subjects has exhibited response to prior therapy with a chemotherapeutic agent. In some such embodiments, the chemotherapeutic agent is a platinum agent. In some embodiments, a platinum-based agent is selected from cisplatin, carboplatin, oxaliplatin, nedaplatin, triplatin tetranitrate, phenanthriplatin, picoplatin, or satraplatin.

In some embodiments, the regimen comprises at least one oral dose of an agent that inhibits PARP (e.g., niraparib). In some embodiments, the regimen comprises a plurality of oral doses. In some embodiments, the regimen comprises once daily (QD) dosing. In some embodiments, an agent that inhibits PARP (e.g., niraparib) is administered on the first day of a 21-day cycle upon completion of infusion with an agent that inhibits PD-1 signaling (e.g., an anti-PD-1 or an anti-PD-L1 antibody agent). In some embodiments, an agent that inhibits PARP (e.g., niraparib) is administered daily throughout the regimen cycle at the same time every day. In some embodiments, the same time every day is in the morning.

In some embodiments, the regimen comprises of one infusion of an agent that inhibits PD-1 signaling (e.g., an anti-PD-1 or an anti-PD-L1 antibody agent) per regimen cycle. In some embodiments, the regimen comprises of one, 30-minute infusion of an agent that inhibits PD-1 signaling (e.g., an anti-PD-1 or an anti-PD-L1 antibody agent) per regimen cycle. In some embodiments, the regimen comprises of one, 30-minute infusion of an agent that inhibits PD-1 signaling (e.g., an anti-PD-1 or an anti-PD-L1 antibody agent) on the first day of each regimen cycle.

In some embodiments, the regimen comprises at least one 2 week-8 week cycle. In some embodiments, the regimen comprises a plurality of 2 week-8 week cycles. In some embodiments, the regimen comprises one 2 week-8 week cycle. In some embodiments, the regimen comprises two 2 week-8 week cycles. In some embodiments, the regimen comprises three or more 2 week-8 week cycles. In some embodiments, the regimen comprises continuous 2 week-8 week cycles.

In some embodiments, the regimen comprises at least one 28 day cycle. In some embodiments, the regimen comprises a plurality of 28 day cycles. In some embodiments, the regimen comprises one 28 day cycle. In some embodiments, the regimen comprises two 28 day cycles. In some embodiments, the regimen comprises three or more 28 day cycles. In some embodiments, the regimen comprises continuous 28 day cycles.

In some embodiments, the regimen comprises at least one 21 day cycle. In some embodiments, the regimen comprises a plurality of 21 day cycles. In some embodiments, the regimen comprises one 21 day cycle. In some embodiments, the regimen comprises two 21 day cycles. In some embodiments, the regimen comprises three or more 21 day cycles. In some embodiments, the regimen comprises continuous 21 day cycles.

In some embodiments, the regimen comprises administration of an effective dose of an agent that inhibits PARP (e.g., niraparib) daily until disease progression or unacceptable toxicity occurs. In some embodiments, the regimen comprises a daily dose of 100 mg, 200 mg, 300 mg or more of a PARP inhibitor (e.g., niraparib) per day dosed until disease progression or unacceptable toxicity occurs. In some embodiments, the range is bounded by a lower limit and an upper limit, the upper limit being larger than the lower limit. In some embodiments, the lower limit may be about 10 mg, about 25 mg, about 50 mg, or about 100 mg. In some embodiments, the upper limit may be about 150 mg, about 200 mg, about 250 mg, about 300 mg, about 350 mg, about 400 mg or about 500 mg. In some embodiments, the oral dose is an amount of a PARP inhibitor (e.g., niraparib) within a range of about 10 mg to about 500 mg. In some embodiments, the dose is within a range of about 25 mg to about 400 mg. In some embodiments, the dose is within a range of about 50 mg to about 300 mg. In some embodiments, the dose is within a range of about 150 mg to about 350 mg. In some embodiments, the dose is within a range of about 50 mg to about 250 mg. In some embodiments, the dose is within a range of about 50 mg to about 200 mg. In some embodiments, the dose is within a range of about 50 mg to about 100 mg. In some embodiments, the dose is within a range of about 100 mg to about 300 mg.

In some embodiments, the oral dose of niraparib is administered in one or more unit dosage forms. In some embodiments, the one or more unit dosage forms are capsules. In some embodiments, each unit dosage form comprises about 100 mg of PARP inhibitor (e.g., niraparib). It is understood that any combination of unit dosage forms can be combined to form a once daily (QD) dose. For example, three 100 mg unit dosage forms can be taken once daily such that 300 mg of PARP inhibitor (e.g., niraparib) is administered once daily. In some embodiments, two 100 mg unit dosage forms can be taken once daily such that 200 mg of PARP inhibitor (e.g., niraparib) is administered once daily In some embodiments, one 100 mg unit dosage forms can be taken once daily such that 100 mg of PARP inhibitor (e.g., niraparib) is administered once daily.

In some embodiments, the regimen comprises a single infusion of at least 200 mg of an agent that inhibits PD-1 signaling (e.g., an anti-PD-1 or an anti-PD-L1 antibody agent). In some embodiments, the regimen comprises a single infusion of an agent that inhibits PD-1 signaling (e.g., an anti-PD-1 or an anti-PD-L1 antibody agent) over a time period of at least 25 minutes, 30 minutes, 35 minutes, 40 minutes, or more. In some embodiments, the range may be bounded by a lower limit and an upper limit, the upper limit being larger than the lower limit. In some embodiments, the lower limit may be about 25 minutes, or about 30 minutes. In some embodiments, the upper limit may be about 35 minutes or about 40 minutes. In some embodiments, the range may be about 25 minutes to about 40 minutes. In some embodiments, the range may be about 25 minutes to about 35 minutes. In some embodiments, the range may be about 25 minutes to about 30 minutes. In some embodiments an agent that inhibits PD-1 signaling (e.g., an anti-PD-1 or an anti-PD-L1 antibody agent) is administered through intravenous (IV) infusion. In some embodiments an intravenous dose of an agent that inhibits PD-1 signaling (e.g., an anti-PD-1 or an anti-PD-L1 antibody agent) is administered in one or more unit dosage forms.

EXAMPLES

The following examples are provided to illustrate, but not limit the claimed invention.

Example 1—Preclinical Evaluation of a PARP Inhibitor in Combination with an Anti-PD-1 or Anti-PD-L1 Agent in Mouse-Derived Syngeneic Transplant Models This example describes the use of mouse-derived syngeneic transplant (MDST) models of various cancer types for evaluating the efficacy of combination treatment with a PARP inhibitor (niraparib) in combination with an anti-PD-1 antibody or anti-PD-L1 antibody.

Methods
In Vitro Experiments

MDA-MB-436 cells were cultured in vitro and treated with 1 μM Niraparib for 48 hours. The cells were subsequently analyzed for expression of Stimulator of Interferon Genes (STING) pathway proteins via Western blotting. In a separate experiment, MDA-MB-436 cells or DLD1 BRCA2−/− cells were treated with 300 nM Niraparib for 24 or 48 hours; cells were subsequently analyzed for gene expression of type-I interferon (IFNB1 or IFNA1).

Animal Models

A panel of 14 syngeneic or humanized xenograft models representing BRCA-proficient (wild-type) and BRCA-deficient (mutant) cancers derived from breast, lung, ovary, skin, sarcoma, bladder and colon tumors was established. The panel included the following genetically engineered mouse tumor models: 1) KrasG12D and PTEN null bladder (BL6078), 2) TP53 null sarcoma (SA9003), 3) MMTV-LPA1 breast (LPA-T22), 4) BRCA1 mutant breast (MDA-MB-436; also referred to as MM-436), 5) APC$^{Min}$ heterozygous mutant skin (SK6005), and 6) BRCA1−/−, TP53−/−, KrasG12D ovarian (BRKras) models. While the bladder syngeneic model was BRCA1 wild-type, the sarcoma model harbored BRCA1 A122E and S123X heterozygous mutations. Specifically, mice were administered treatments after tumors reached 50-150 mm$^3$. Niraparib was administered at 50 mg/kg full dose or at a suboptimal dose (25-35 mg/kg) orally once daily. The suboptimal dose administered for specific tumor models was as follows: 35 mg/kg daily for 5 consecutive days per week (QD×5/week) for the BR1126 tumor model, 35 mg/kg (QD×5/week) for the MDA-MB-436 tumor model, 30 mg/kg for the BRKras tumor model, and 25 mg/kg daily for the SK6005 tumor model. The anti-PD-1 antibody (RMP1-14/2C4) or the anti-PD-L1 antibody (10F.9G2) was administered twice weekly intraperitoneally at 10 mg/kg dose unless otherwise noted. For the MDA-MB-436 model, the anti-PD-1 antibody (pembrolizumab) was administered intraperitoneally at a 200 mg dose on days 0, 4, 9, 13, 19, 22, and 28. For the SK6005 model, the anti-PD-1 antibody (RMP1-14) was administered twice weekly intraperitoneally at 5 mg/kg dose. Tumor growth was monitored twice per week.

Study Endpoint

The major endpoints of the study included tumor growth inhibition (TGI) analysis, which is an indication of antitumor effectiveness, and is expressed as:

TGI(%)=100×(1−ΔT/ΔC), where:

ΔT=mean tumor volume of the drug-treated group on a given day of the study-mean tumor volume of the drug-treated group on the initial day of dosing ΔC=mean tumor volume of the control group on a given day of the study-mean tumor volume of the control group on the initial day of dosing.

Additionally. the ΔT/ΔC value (%) was an indicator of tumor response to treatment, and was used as an anti-tumor activity endpoint.

Other criteria of endpoints for the experimental animals included one or more of the followings: severe dehydration; impaired mobility (not able to eat or drink); ananastasia, continuous prone or lateral position; hypoactivity, signs of muscular atrophy; effort respiration; progressive hypothermia; paralytic gait, clonic convulsions, tonic convulsions; persistent bleeding from the openings; unable to move normally due to enlarged tumor mass; unable to move normally due to significant ascites and enlarged abdomen; tumor volume exceeding 3000 mm$^3$ or mean tumor volume of the group over 2000 mm$^3$; and opened tumor ulcerations of approximately 25% or greater of the surface of the tumor.

At the end of the study, tumors were collected and cut into fragments where some fragments were reserved for snap freezing and other tumor fragments were subjected to formalin fixation and paraffin embedding (FFPE).

Results

Figure 1B:
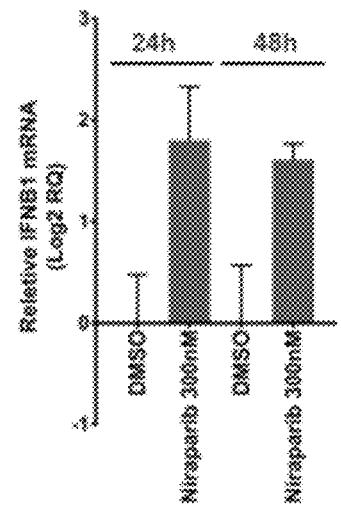
FIG. 1B depicts mRNA expression of IFNB1 in MDA-MB-436 cells following Niraparib treatment.
Figure 1C:
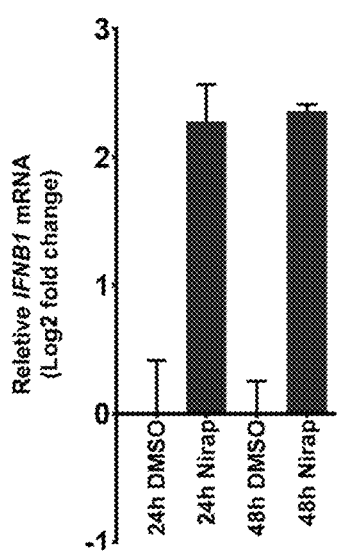
FIG. 1C depicts mRNA expression of IFNB1 in DLD1 BRCA2−/− cells following Niraparib treatment.
Figure 1D:
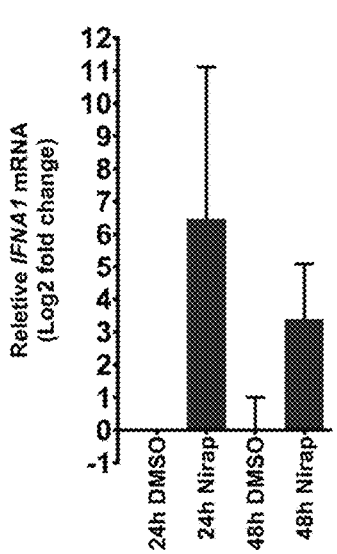
FIG. 1D depicts mRNA expression of IFNA1 in DLD1 BRCA2−/− cells following Niraparib treatment.
Figure 1E:
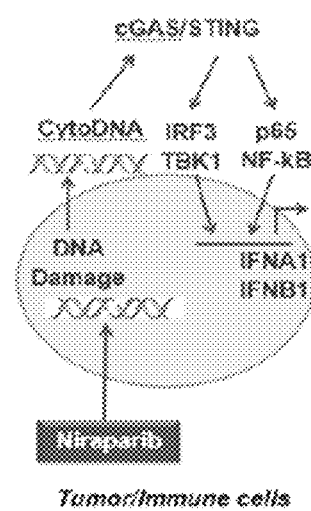
FIG. 1E is a schematic diagram of the cGAS/STING signaling pathway upon activation due to DNA damage.

In vitro analysis of MDA-MB-436 cells indicated expression of STING pathway proteins, such as p-STING (Ser366), STING, p-TBK1 (Ser172), TBK1, p-NF-κB p65, and NF-κB p65upon treatment with Niraparib (FIG. 1A). Additionally, mRNA expression of type-I interferon (IFNB1) was detected in MDA-MB-436 cells following Niraparib treatment (FIG. 1B). mRNA expression of type-I interferon (IFNB1 or IFNA1) was also detected in DLD1 BRCA2−/− cells following Niraparib treatment (FIG. 1C and FIG. 1D). These data indicate that Niraparib can activate the cGAS/STING pathway via a DNA damage stimulus to induce type-I interferon expression as shown in FIG. 1E.

Figure 2:
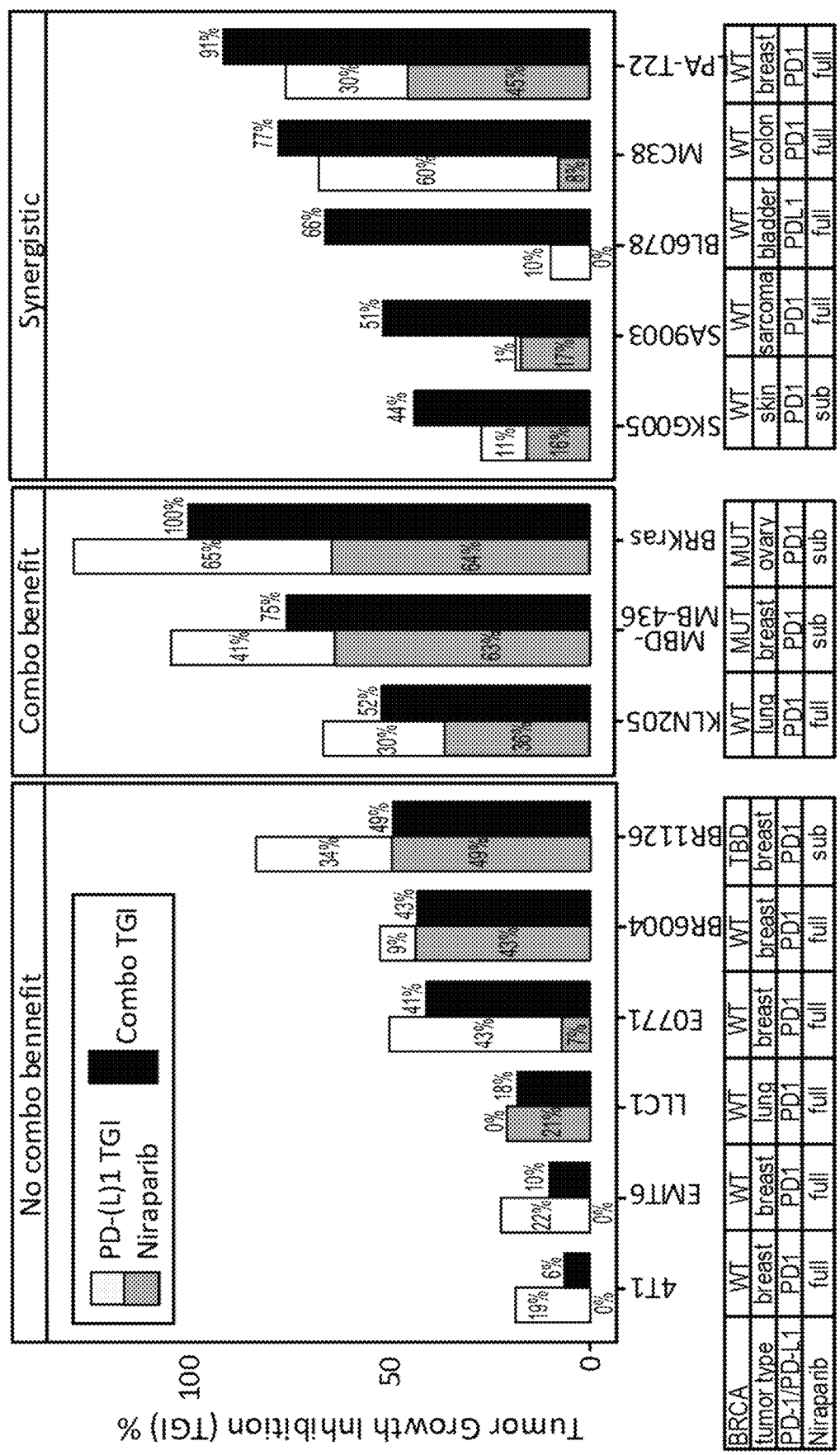
FIG. 2 depicts tumor growth inhibition (TGI) due to treatment with Niraparib alone, anti-PD-1 or anti-PD-L1 alone, and a combination of Niraparib and anti-PD-1 or anti-PD-L1 in a panel of syngeneic or humanized xenograft cancer models. The PD-1 inhibitor resulted in 0% TGI for LLC1.
Figure 3A:
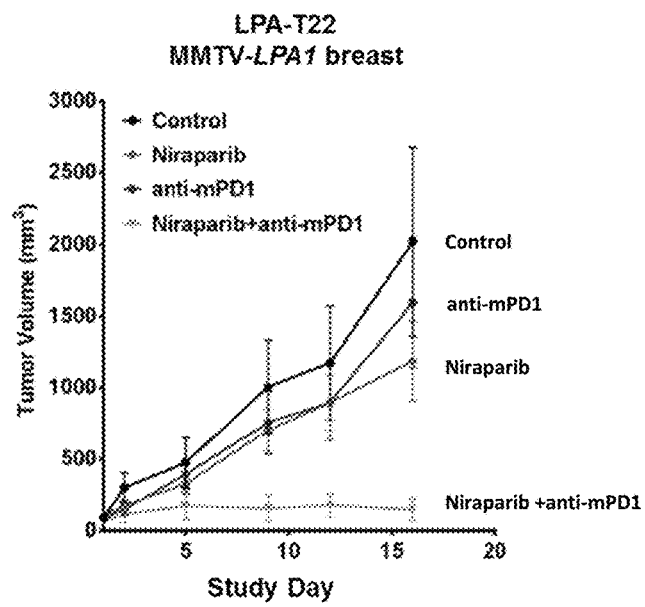
FIG. 3A-FIG. 3E depicts evaluation of treatment efficacy based on tumor volume in a syngeneic MMTV-LPA1 breast model (FIG. 3A), Kras G12D and PTEN null bladder model (FIG. 3B), TP53 null sarcoma model (FIG. 3C), BRCA1 mutant breast model (FIG. 3D), and APC$^{Min}$ heterozygous mutant skin model (FIG. 3E).
Figure 3B:
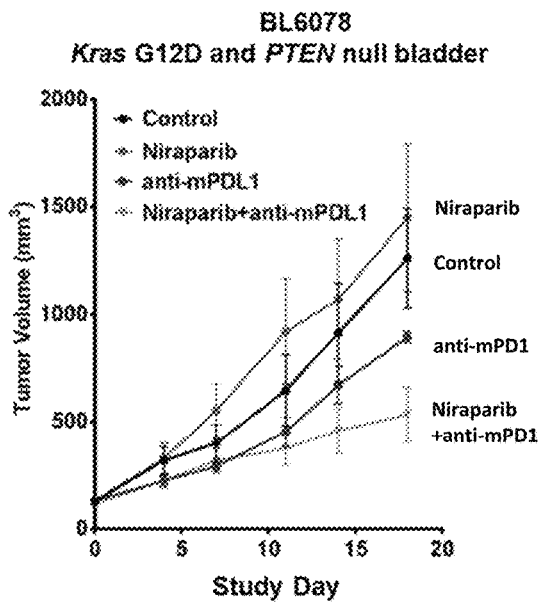
Figure 3C:
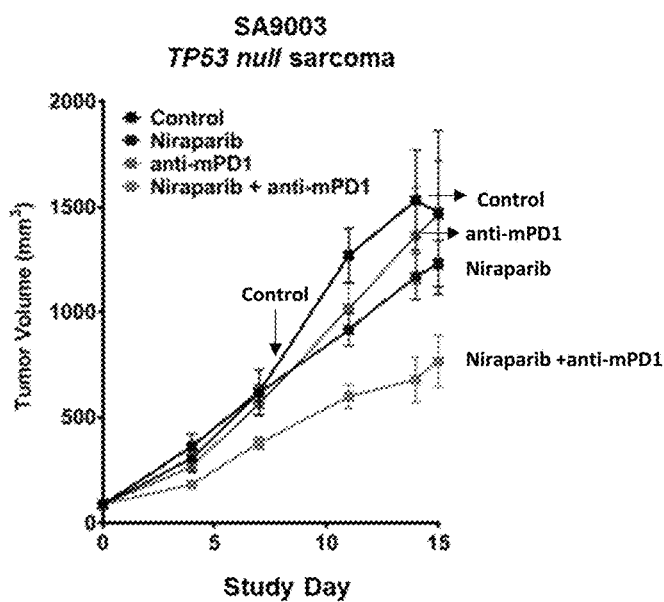
Figure 3D:
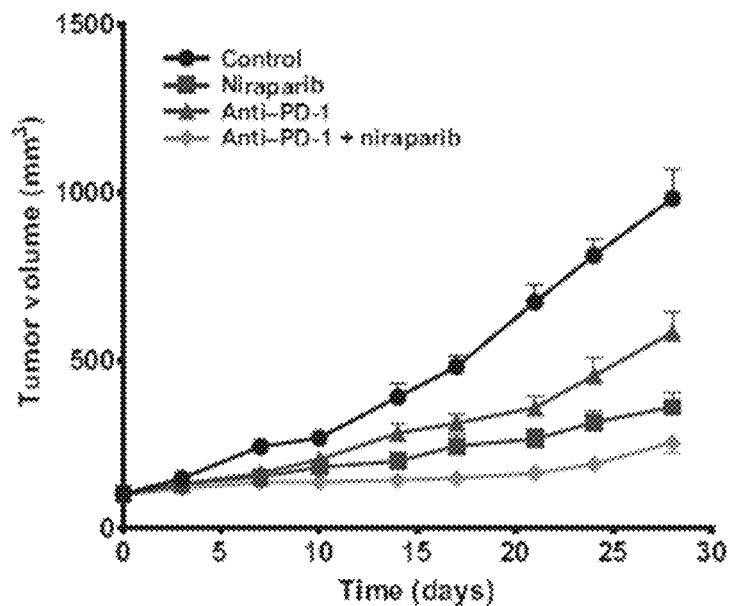
Figure 3E:
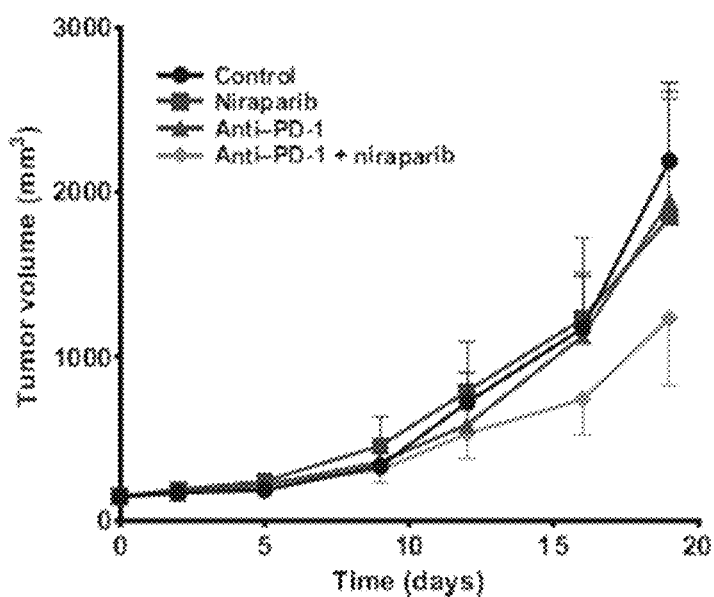

A panel of 14 syngeneic or humanized xenograft models was then screened for efficacy of Niraparib treatment alone, anti-PD-1 or anti-PD-L1 treatment alone, and combination treatment of Niraparib and anti-PD-1 or anti-PD-L1 (FIG. 2). Synergistic anti-tumor responses from combination treatment of Niraparib and anti-PD-1 or anti-PD-L1 were observed in 5/11 BRCA proficient models Overall, enhanced antitumor activity from the combination treatment was present in 8/14 models, including both BRCA proficient and BRCA deficient models. Synergistic tumor growth inhibition was observed in BRCA proficient syngeneic (1) MMTV-LPA1 breast (LPA-T22); (2) Kras G12D and PTEN null bladder (BL6078); and (3) TP53 null sarcoma (SA9003) models (FIG. 3A-FIG. 3C). Synergistic tumor growth inhibition was also observed in BRCA1 mutant breast (MDA-MB-436) (FIG. 3D), and BRCA proficient APC$^{Min}$ heterozygous mutant skin (SK6005) (FIG. 3E) models.

These BRCA proficient syngeneic models were either partially sensitive or refractory to anti-PD-1 or anti-PD-L1 monotherapies, which led to no more than 30% of average tumor growth inhibition (TGI). However, synergistic antitumor activities were observed in all three models when combining niraparib with anti-PD-1 or anti-PD-L1 antibodies. In MMTV-LPA1 T22 model, single-agent niraparib and anti-PD-1 antibody resulted in 45% and 30% TGI, respectively, whereas their combination was synergistically effective resulting in 91% average TGI. In the TP53 null sarcoma model, which is refractory to single agent niraparib (TGI=1%) and anti-PD-1 antibody (TGI=17%), combination synergy was also observed (TGI=51%). The Kras G12D and PTEN null bladder model was neither responsive to niraparib monotherapy nor sensitive to anti-PD-1 antibody (TGI=10%), whereas their combination led to 66% average TGI. Overall, synergistic tumor growth inhibition from the combination treatment of Niraparib and anti-PD-1 or anti-PD-L1 was observed in each of the BRCA-proficient syngeneic tumor models.

Figure 4A:
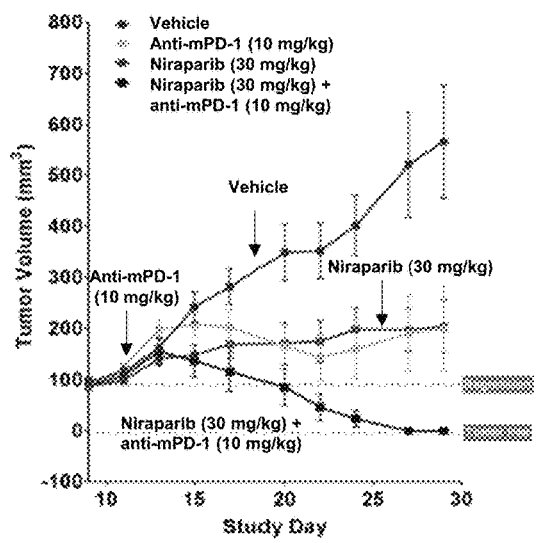
FIG. 4A depicts treatment efficacy of 30 mg/kg Niraparib and 10 mg/kg anti-PD-1 based on tumor volume in a syngeneic BRCA1 null, TP53 null, and Kras G12D ovarian model.
Figure 4B:
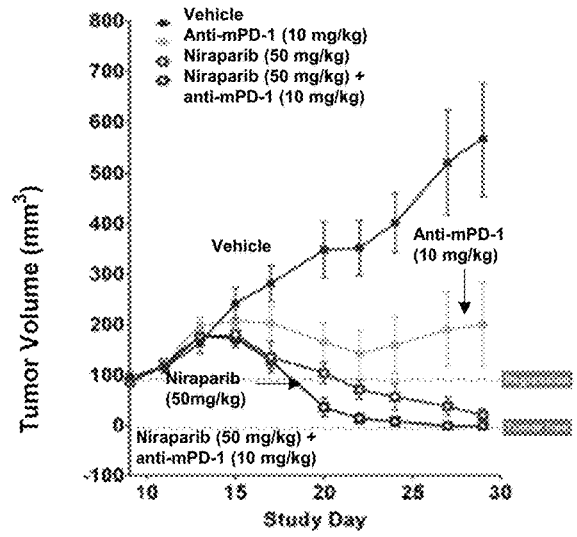
FIG. 4B depicts treatment efficacy of 50 mg/kg Niraparib and 10 mg/kg anti-PD-1 based on tumor volume in a syngeneic BRCA1 null, TP53 null, and Kras G12D ovarian model.
Figure 4C:
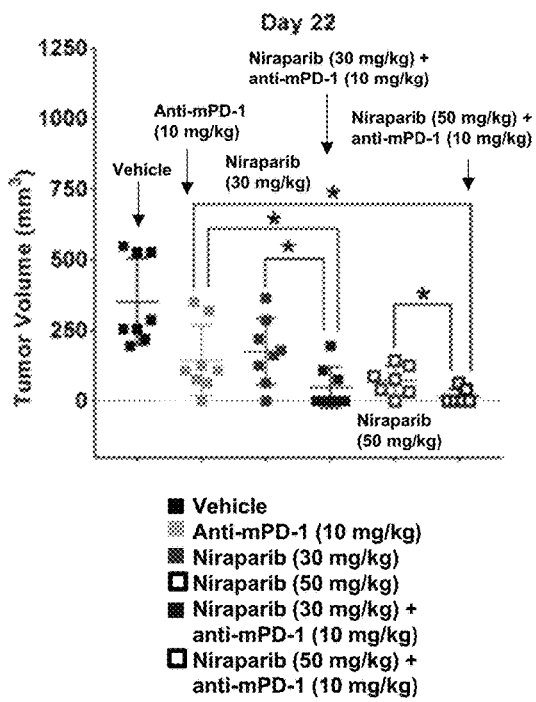
FIG. 4C depicts scatter plot measurements of individual tumor volumes on day 22.
Figure 4D:
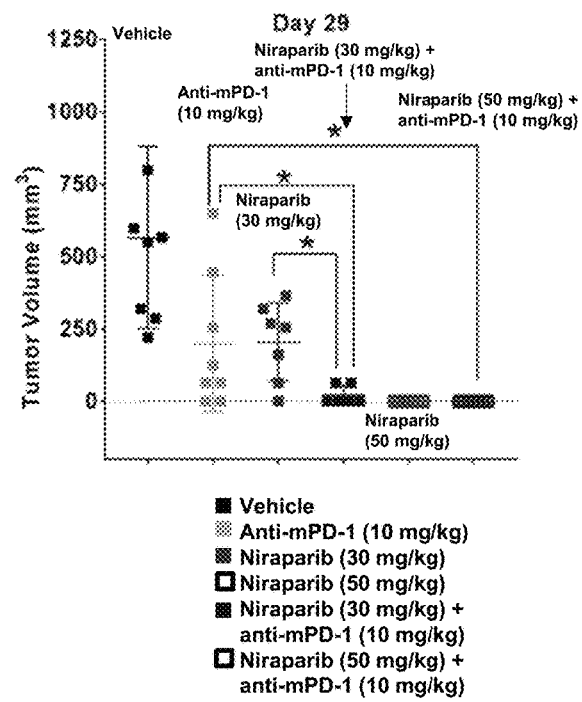
FIG. 4D depicts scatter plot measurements of individual tumor volumes on day 29.
Figure 4E:
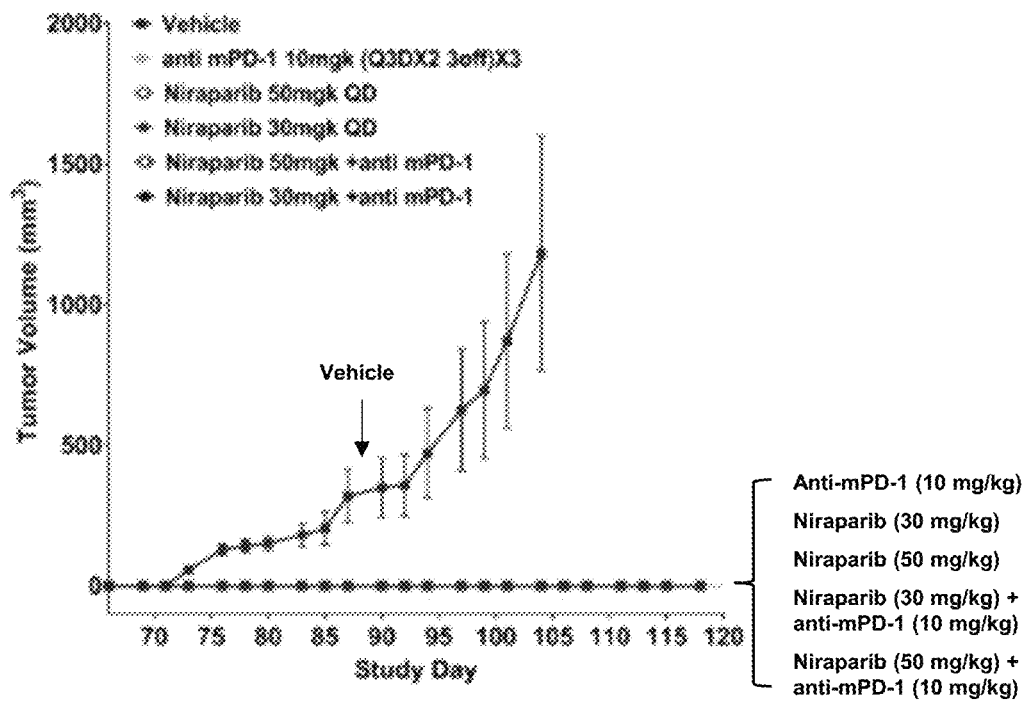
FIG. 4E depicts tumor growth in tumor-free mice as a result of treatment following re-challenge with tumor cells on day 65.
Figure 4F:
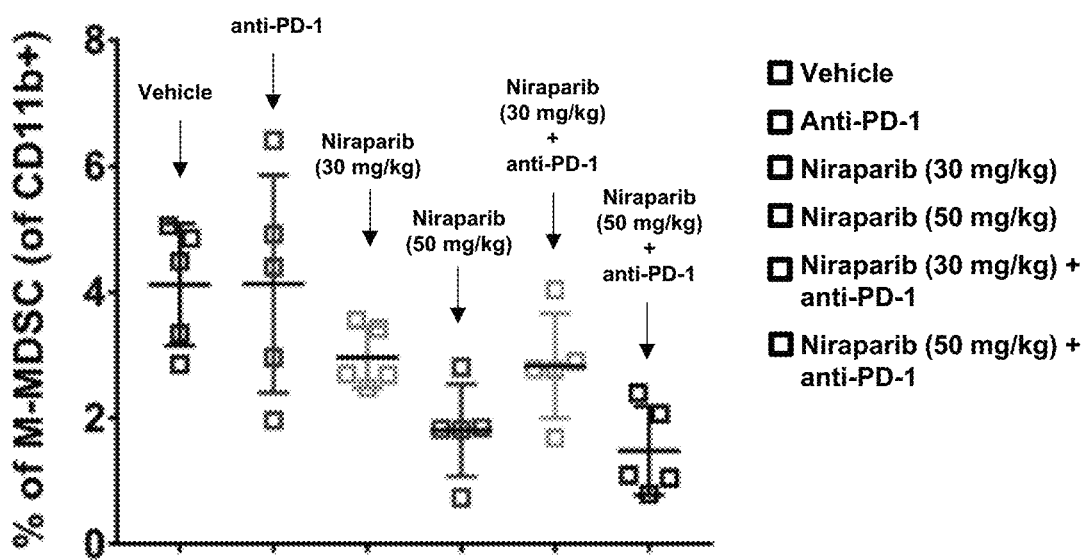
FIG. 4F depicts the percentage of monocytic myeloid-derived suppressor cells (M-MDSCs) in the CD11b+ tumor cell population upon 7 days of treatment.

Next, the BRCA−/−, TP53−/−, KrasG12D ovarian cancer mouse syngeneic model (BRKras) was treated with Niraparib, anti-PD1, or a combination of Niraparib and anti-PD-1 for 21 days (day 9 to day 29). Tumor regrowth was monitored post-treatment (day 29 to day 64) as shown in FIG. 4A-FIG. 4D. Niraparib was administered at 30 mg/kg (FIG. 4A) or 50 mg/kg (FIG. 4B) and individual tumor volumes on day 22 and day 29 are shown in FIG. 4C and FIG. 4D, respectively. Statistical significance was determined using a p-value <0.05 by a student's t-test. Table 2 summarizes the ratio of mice with a palpable tumor on day 29 (last treatment day) and the ratio of mice with tumor growth observed from day 30 to day 64. None of the tumor-free mice demonstrated tumor regrowth post-day 29. Finally, tumor growth was measured in tumor-free mice following re-challenge with BRKras tumor cells on day 65 (FIG. 4E). With the exception of the age-matched control group, none of treatment groups displayed a palpable tumor upon re-challenge from day 65 to day 118. Finally, as shown in FIG. 4F, the combination of 50 mg/kg Niraparib and anti-PD-1 resulted in a smaller percent (on average) of monocytic myeloid-derived suppressor cells (M-MDSCs) in the CD11b+ tumor cell population upon 7 days of treatment compared to any other cohort.

TABLE 2

Ratio of mice with palpable tumor or tumor growth.

| Group | Ratio of mice with palpable tumor on last day of treatment (day 29) | Ratio of mice with tumor growth during observation (day 30-day 64) |
| --- | --- | --- |
| Vehicle | 8/8 | 6/8 |
| anti PD-1 | 6/8 | 3/8 |
| Niraparib (50 mg/kg) | 2/6 | 1/6 |
| Niraparib (30 mg/kg) | 6/7 | 6/7 |
| Niraparib (50 mg/kg) + anti-mPD-1 | 0/7 | 0/7 |
| Niraparib (30 mg/kg) + anti-mPD-1 | 0/7 | 0/7 |

CONCLUSION

Niraparib treatment alone activates the cGAS/STING pathway and induces type-I interferon expression. Additionally, the combination of Niraparib and anti-PD-1/anti-PD-L1 treatment was well-tolerated in xenograft tumor models. Notably, the combination of Niraparib and anti-PD-1 enhanced anti-tumor activity and increased the durability of responses in a BRCA1-null ovarian cancer syngeneic model.

Overall, Niraparib and anti-PD-1/anti-PD-L1 combination demonstrated therapeutic anti-tumor activities as compared to niraparib or anti-PD-1/anti-PD-L1 monotherapy in both BRCA proficient and BRCA deficient tumor models. Importantly, synergistic tumor growth inhibition was observed in multiple BRCA proficient tumor models. These findings indicate that a Niraparib and anti-PD-1 combination or a Niraparib and anti-PD-L1 combination can benefit both BRCA-deficient and BRCA-proficient patient populations.

EQUIVALENTS

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

What is claimed is:

1. A method of treating ovarian cancer, fallopian tube cancer, peritoneal cancer, breast cancer, or sarcoma in a subject, the method comprising:
   administering a therapeutically effective amount of an agent that inhibits poly[ADP-ribose] polymerase (PARP) and an agent that inhibits programmed death-1 protein (PD-1) signaling to the subject,
   wherein the ovarian cancer, fallopian tube cancer, peritoneal cancer, breast cancer, or sarcoma is associated with one or more mutations in one or more of the following genes: Kras, PTEN, TP53, Apc, and/or is associated with overexpression of LPA1;
   wherein the agent that inhibits PARP is niraparib or a salt thereof; and
   wherein the agent that inhibits programmed death-1 protein (PD-1) signaling is pembrolizumab or TSR-042.

2. The method of claim 1, wherein the ovarian cancer, fallopian tube cancer, peritoneal cancer, breast cancer, or sarcoma is associated with mutations in at least two of the following genes: Kras, PTEN, TP53, or Apc, wherein each mutated gene comprises one or more mutations.

3. The method of claim 1, wherein the agent that inhibits PD-1 signaling is pembrolizumab.

4. The method of claim 1, wherein the agent that inhibits PD-1 signaling is TSR-042.

5. The method of claim 1, wherein the subject has previously been treated with one or more different cancer treatment modalities.

6. The method of claim 5, wherein the subject has previously been treated with one or more of radiotherapy, chemotherapy or immunotherapy.

* * * * *